United States Patent
Giakos

(10) Patent No.: US 7,420,675 B2
(45) Date of Patent: *Sep. 2, 2008

(54) MULTI-WAVELENGTH IMAGING SYSTEM

(75) Inventor: George Giakos, Fairlawn, OH (US)

(73) Assignee: The University of Akron, Akron, OH (US)

( * ) Notice: Subject to any disclaimer, the term of this patent is extended or adjusted under 35 U.S.C. 154(b) by 262 days.

This patent is subject to a terminal disclaimer.

(21) Appl. No.: 11/129,769

(22) Filed: May 13, 2005

(65) Prior Publication Data

US 2005/0264813 A1 Dec. 1, 2005

Related U.S. Application Data

(63) Continuation-in-part of application No. PCT/US2004/015046, filed on May 13, 2004.

(60) Provisional application No. 60/482,386, filed on Jun. 25, 2003, provisional application No. 60/665,773, filed on Mar. 28, 2005.

(51) Int. Cl.
*G01J 4/00* (2006.01)
(52) U.S. Cl. ........................ 356/364; 356/367
(58) Field of Classification Search .............. 356/33, 356/364–370
See application file for complete search history.

(56) References Cited

U.S. PATENT DOCUMENTS

| | | | | |
|---|---|---|---|---|
| 5,129,724 A | * | 7/1992 | Brophy et al. | 356/503 |
| 5,216,433 A | | 6/1993 | Kurtz | |
| 5,247,176 A | | 9/1993 | Goldstein | |
| 5,521,705 A | * | 5/1996 | Oldenbourg et al. | 356/368 |
| 5,606,546 A | * | 2/1997 | Best et al. | 369/275.1 |
| 5,788,632 A | * | 8/1998 | Pezzaniti et al. | 600/316 |
| 5,850,284 A | | 12/1998 | Schoeffler et al. | |
| 6,204,924 B1 | * | 3/2001 | Cyr | 356/453 |
| 6,207,924 B1 | * | 3/2001 | Cyr | 356/463 |
| 6,316,773 B1 | | 11/2001 | Giakos | |

(Continued)

FOREIGN PATENT DOCUMENTS

WO  WO 02/19381 A1  3/2002

OTHER PUBLICATIONS

Smith, Matthew H., Optimization of a dual-rotating-retarder Mueller matrix polarimeter, Applied Optics, May 1, 2002, pp. 2488-2493, vol. 41, No. 13.

Demos, S.G., et al., Deep Subsurface Imaging in Tissues Using Spectral & Polarization Filtering, Optic Express, Jul. 2000, pp. 23-28, vol. 7, No. 1.

(Continued)

*Primary Examiner*—L. G. Lauchman
*Assistant Examiner*—Jarreas C Underwood
(74) *Attorney, Agent, or Firm*—Roetzel & Andress; George W. Moxon, II

(57) ABSTRACT

The present invention relates to a multi-energy system that generates and/or forms images of targets/structures by applying Mueller matrix imaging principles and/or Stokes polarimetric parameter imaging principles to data obtained by the multi-energy system. In one embodiment, the present invention utilizes at least one energy or light source to generate two or more Mueller matrix and/or Stokes polarization parameters images of a target/structure, and evaluates the Mueller matrix/Stokes polarization parameters multi-spectral difference(s) between the two or more images of the target/structure. As a result, high contrast, high specificity images can be obtained. Additional information can be obtained by and/or from the present invention through the application of image, Mueller matrix decomposition, and/or image reconstruction techniques that operate directly on the Mueller matrix and/or Stokes polarization parameters.

30 Claims, 6 Drawing Sheets

U.S. PATENT DOCUMENTS

| | | | |
|---|---|---|---|
| 6,384,916 B1 * | 5/2002 | Furtak | 356/369 |
| 6,567,678 B1 | 5/2003 | Oosta | |
| 6,618,145 B1 | 9/2003 | Goldstein | |
| 6,636,582 B2 | 10/2003 | Rader | |
| 6,643,021 B1 | 11/2003 | Kawamura | |
| 6,683,934 B1 | 1/2004 | Zhao et al. | |
| 6,762,829 B2 * | 7/2004 | Babin et al. | 356/73.1 |
| 6,927,888 B2 * | 8/2005 | Garcia et al. | 359/196 |
| 7,002,685 B2 * | 2/2006 | Wang | 356/364 |
| 7,022,685 B2 * | 2/2006 | Wang | 356/364 |
| 7,061,614 B2 * | 6/2006 | Wang et al. | 356/369 |
| 2004/0012853 A1 | 1/2004 | Garcia et al. | |

OTHER PUBLICATIONS

Chenault, D.G., et al., Mueller Matrix Algorithms, SPIE, 1992, pp. 231-246, vol. 1746.

A Azzam, R.M., Photopolarimetric Measurement of the Mueller Matrix by Fourier Analysis of a Single Detected Signal, Optics Letters, 1978, pp. 148-150, vol. 2, No. 6.

Goldstein, D.H., et al., Near Infrared Imaging Polarimetry, SPIE, 2002, vol. 4481, p. 100.

Chenault, D.B., et al., Polarization Imaging through Scattering Media, SPIE, 2000, vol. 4133, p. 124.

Lu, S., et al., Interpretation of Mueller Matrices Based on Polar Decomposition, J. of Opt. Soc. Am., May 1996, vol. 13, No. 5 pp. 1106-1113.

* cited by examiner

MULTI-WAVELENGTH IMAGING SYSTEM

RELATED APPLICATION DATA

This application is both a continuation-in-part of PCT Application Number PCT/US2004/015046, which designated the United States and was filed on May 13, 2004, and was published as WO 2004/029015, which claims priority to U.S. patent application No. 60/482,386, filed Jun. 25, 2003, and a continuation of U.S. Provisional Patent Application No. 60/665,773, filed Mar. 28, 2005. All of the above-mentioned applications are hereby incorporated by reference in their entireties.

FIELD OF THE INVENTION

The present invention relates to a multi-energy system that generates and/or forms images of targets/structures by applying Mueller matrix imaging principles and/or Stokes polarimetric parameter imaging principles to data obtained by the multi-energy system. In one embodiment, the present invention utilizes at least one energy or light source to generate two or more Mueller matrix and/or Stokes polarization parameters images of a target/structure, and evaluates the Mueller matrix/Stokes polarization parameters multi-spectral difference(s) between the two or more images of the target/structure. As a result, high contrast, high specificity images can be obtained. Additional information can be obtained by and/or from the present invention through the application of image, Mueller matrix decomposition, and/or image reconstruction techniques that operate directly on the Mueller matrix and/or Stokes polarization parameters.

BACKGROUND OF THE INVENTION

The ability to measure the Mueller matrix and/or the Stokes parameters of a target or a structure, and form images based on them, and then obtain their spectral image difference (dual-energy image subtraction), can provide significant insight on the sample/target composition. Such measurements can also reveal significant structural or molecular information that cannot be obtained via conventional imaging techniques. As a result, high-signal-to-background ratio, leading to an enhanced specificity, and high contrast images could be obtained by any imaging system that could apply the above principles. Furthermore, information could also be obtained by applying Mueller matrix decomposition, image-processing, neural-fuzzy logic algorithms and image reconstruction techniques that operate directly on the Mueller matrix and/or the Stokes polarization parameters.

The present invention is referred interchangeably through out the text as "Mueller Matrix/Stokes Parameters Polarimetric Spectral Difference Imaging" or "Mueller Matrix/Stokes Parameters Polarimetric Dual-Energy Imaging", without loss of meaning, since it leads to the formation of several Mueller matrix polarimetric difference images and/or Stokes polarization parameter image differences, formed by pairs of Mueller matrix polarimetric images/Stokes polarization parameter images, acquired at at least two distinct wavelengths, chosen from a wavelength spectrum $\lambda_1, \ldots \lambda_n$. Therefore, multiple spectral polarimetric image differences can be obtained.

The present invention initially acquires images based on Mueller matrix and/or Stokes polarization parameter formalism/imaging principles through the interrogation of targets with multiple wavelengths. The present invention then subtracts these images, acquired at at least two different wavelengths to yield multi-wavelength (multi-spectral) polarimetric image differences. In other words, in one embodiment the present invention permits the fusing of multi-spectral difference detection principles with Mueller matrix and/or Stokes polarization parameter imaging principles. Further imaging information about the target/structure can be/is obtained by Mueller matrix polar decomposition of the images at different wavelengths and forming image differences at at least two wavelengths.

In fact, Mueller matrix measurements permit parameters such as diattenuation, retardance, depolarization power, and birefringence to be obtained. The importance of these parameters can be enhanced further under multi-spectral interrogation of the target/structure, providing useful information regarding the nature of the target/structure. For instance, interrogation of biological structures with multiple wavelengths, leads in practice to a multilayer interrogation of tissue, allowing one to obtain high-contrast images at different depths. This allows one to differentiate tumor and cancerous structures or cells from healthy ones based on a change in tissue birefringence. Therefore, a subtraction of the birefringence obtained at at least two distinct wavelengths can enhance the structure of interest, removing the influence of the interfering tissue or cells. Therefore subtraction of the diattenuation, retardance, depolarization power, and birefringence at distinct wavelengths, under multi-spectral interrogation of the target/structure can provide insightful structural and physiological information based on the difference of the attenuation of amplitude of the incident light, phase change difference, depolarizing potential of the target difference, and phase shift difference, due to the variation of the index of refraction, obtained at at least two distinct wavelengths, respectively.

The principles of the multi-fusion multi-spectral-dual-rotating retarder, dual-energy complete polarimeter, are shown in FIG. 1. However, the present invention can be applied to any theoretical or experimental technique that estimates the full-16 element Mueller matrix of the system (target/associated optics), and relates, therefore, the output Stokes parameters to the input Stokes parameters.

The principles multi-spectral Mueller matrix polarimetric image difference and/or Stokes polarization parameters image difference involve, in one instance, the acquisition of multi-wavelength optical Mueller matrix/Stokes polarimetric images. In one embodiment, a weighted subtraction of two Mueller matrix images, produced from a high energy (low wavelength) and another from a low energy (high wavelength) energy and/or light source can produce a polarimetric Mueller matrix/Stokes polarimetric image difference, which eliminates interfering background structure, as well as it enhances the polarization-based amplitude contrast information (diattenuation property of the target/structure), and polarization-based phase contrast information (birefringence property of the target/structure).

Polarimetric imaging offers distinct advantages for a wide range of detection and classification problems.

Polarimetric imaging relies on the preservation of polarization of backscattered light, while offering distinct signatures related to surface smoothness, orientation, and target/structure composition. Under certain circumstances, the polarization of the scattered light depends upon a number of geometrical, and physical parameters, such as incident polarization state, shape, size, and concentration of the scatterer, or more generally from the refractive indexes of the scatterer and the surrounding medium. Specifically, it relies on the assumption that weakly scattered light maintains its initial polarization state, while highly scattered light does not maintain its initial polarization state. In one embodiment, the present invention permits the use additional polarimetric-sensitive signatures, such as scattering, due to different concentration of the scatterer, size, and other variables to be obtained under multiple wavelength interrogation, and subsequently used to form a polarimetric image difference.

SUMMARY OF THE INVENTION

In one embodiment, the present invention operates on lightwave multi-spectral, multi-fusion, multifunctional, Muller matrix/Stokes polarization parameters imaging principles. It is capable of interrogating targets, structures or samples with multiple wavelengths in order to form multi-spectral Mueller matrix/Stokes polarimetric images, obtained at different wavelengths, and then obtain their spectral image difference (dual-energy image subtraction). The use of two Mueller matrix polarimetric optical images, one produced from a high energy (small wavelength) and another from a low energy (large wavelength) laser beams, and the subsequent subtraction of these two images, can produce a high-contrast polarimetric energy image difference which eliminates or minimizes interfering background and clutters, or enhances the image process. Further image enhancement can be achieved by subtracting Stokes polarimetric parameter images and the like, obtained at different optical wavelengths, such as degree of linear polarization images (DOLP)'s, forming Stokes polarimetric parameter spectral image differences.

These image images can be further manipulated, or combined, to enhanced the detection process. As a result, the present invention can provide both spectral and polarimetric information. Furthermore, decomposition of the Mueller matrix images, at different optical wavelengths result in enhanced polarization-based amplitude contrast information (diattenuation property of the target), polarization-based phase contrast information (birefringence property of the target), and depolarization contrast, due to the formation of image differences using different distinct wavelengths. This data gives rise to Muller matrix polarimetric difference images obtained at different wavelengths, which contain polarization-based amplitude contrast and phase contrast information. These principles apply not only to the interrogation of multiple targets, aimed at the removal of interfering structures, but also single targets as well, giving rise to enhanced energy, spectral and polarimetric contrast, namely, polarization-based amplitude contrast, depolarization intensity contrast, and phase contrast information.

The present invention relies in part on the following relationships: subtraction of two Mueller matrix polarimetric images $M_{\lambda 1}$, $M_{\lambda 2}$ of a target, structure and/or sample, obtained at least two distinct wavelengths $\lambda_1$, $\lambda_2$:

| | |
|---|---|
| $M_{\lambda 2} - M_{\lambda 1}$ | [1] Mueller matrix of the target (M) |
| $D_2 - D_1$ | [2] Diattenuation of the target (D) |
| $M_{D\lambda 2} - M_{D\lambda 1}$ | [3] Diattenuation matrix ($M_D$) |
| $M_{R\lambda 2} - M_{R\lambda 1}$ | [4] Retardance matrix ($M_R$) |
| $M_{\Delta\lambda 2} - M_{\Delta\lambda 1}$ | [5] Depolarizing matrix ($M_\Delta$) |
| $\delta_{\lambda 2} - \delta_{\lambda 1}$ | [6] Birefringence ($\delta$) |
| $S_{j\lambda 2} - S_{j\lambda 1}$ | [7] Stokes Parameters ($S_j$), where j = 0, 1, 2, 3 |
| $(DOP)_{\lambda 2} - (DOP)_{\lambda 1}$ | [8] Degree of polarization (DOP) |
| $(DOLP)_{\lambda 2} - (DOLP)_{\lambda 1}$ | [9] Degree of linear polarization (DOLP) |
| $(DOCP)_{\lambda 2} - (DOCP)_{\lambda 1}$ | [10] Circular polarization (DOCP) |
| $(e)_{\lambda 2} - (e)_{\lambda 1}$ | [11] Ellipticity |
| $(\eta)_{\lambda 2} - (\eta)_{\lambda 1}$ | [12] Azimuth |
| $(\epsilon)_{\lambda 2} - (\epsilon)_{\lambda 1}$ | [13] Eccentricity |

(the order of the above operations can be reversed (i.e., $\lambda 1 - \lambda 2$)), where subscripts 1 and 2 refer to any Mueller matrix matrices, in one instance polarimetric matrices, acquired through multi-spectral interrogation of the target with wavelengths $\lambda_1$ and $\lambda_2$, respectively, chosen from a spectrum $\lambda_1, \ldots \lambda_n$. Any number of Mueller matrices can be generated using the appropriate number of interrogating wavelengths (e.g., n Muller matrices can be generated using n interrogating wavelengths). By subtracting the 16 Mueller matrix elements of one matrix, acquired at one wavelength, one by one from those acquired at one or more different wavelengths (e.g., $m_{11\lambda 2} - m_{11\lambda 1}$) and so on, significant information regarding the nature of the target can be achieved. In general, multiple wavelengths can be utilized to interrogate the target. Further exploitation and arithmetic manipulation of S0, S1, S2, S3, obtained at different wavelengths, such as subtraction, addition, multiplication, division or combination thereof, can enhance the image process, giving rise to Stokes polarization parameters differences and the like.

The foregoing relationships can be further manipulated to enhance birefringence properties of the target; enhance diattenuation properties of the target; enhance depolarization intensity contrast; maximize spectral and energy information of the target and the surroundings; reduce interfering structures or background, leading therefore to: enhance detectability; target, structure and/or sample identification, discrimination, and classification; enhanced contrast and spatial resolution; specificity of targets embedded in turbid media, cluttered targets or samples embedded or surrounded by complex surroundings, low-contrast targets or samples, or under harsh illumination conditions such as very low/very strong light illumination or mixed light conditions, and background.

In one embodiment, the present invention relates to a multi-energy polarization imaging system comprising: (a) at least one energy source for irradiating a target with at least one quantity of light and at least one quantity of energy, the at least one quantity of light comprising at least one wavelength of light and the at least one quantity of energy comprising at least one wavelength of energy, wherein the wavelength of the energy is either shorter or longer than the wavelength of the at least one quantity of light; (b) a polarization-state generator for generating a polarization state for each quantity of light, the polarization-state generator comprising at least one polarizer, each polarizer being adapted to polarize an individual wavelength before the one or more quantities of light enter at least one first waveplate; (c) a polarization-state receiver for evaluating a resulting polarization state of each of the one or more quantities of light following illumination of the target, the polarization-state receiver comprising at least one second waveplate through which the one or more quantities of light are transmitted before entering at least one second polarizer; (d) an image-capture device for capturing at least a first image and a second image of the target irradiated by the at least one quantity of light and the at least one quantity of energy, the first image corresponding to an image of the target generated from the wavelength of light and the second image corresponding to an image of the target generated from the wavelength of energy; and (e) a processing unit for assigning a weighting factor to at least one of the first and second images and evaluating a weighted difference between the first and second images to generate a multi-wavelength image of the target.

In another embodiment, the present invention relates to a multi-energy polarization imaging system comprising: (i) at least one light source for illuminating a target with at least one quantity of light, the at least one quantity of light comprising at least two wavelengths of light, a first wavelength and a second wavelength, the second wavelength being different than the first wavelength; (ii) a polarization-state generator for generating a polarization state for each quantity of light, the polarization-state generator comprising at least two polarizers, each polarizer being adapted to polarize an individual wavelength before the one or more quantities of light enter at least one first waveplate; (iii) a polarization-state receiver for evaluating a resulting polarization state of each of the one or more quantities of light following illumination of the target, the polarization-state receiver comprising at least one second waveplate through which the one or more quantities of light are transmitted before entering at least one second polarizer; (iv) an image-capture device for capturing at least a first image and a second image of the target illuminated by the at least one quantity of light, the first image corresponding to an image of the target generated from the first wavelength component of the at least one quantity of light and the second image corresponding to an image of the target generated from the second wavelength component of the at least one quantity of light; and (v) a processing unit for assigning a weighting factor to at least one of the first and second images and evaluating a weighted difference between the first and second images to generate a multi-wavelength image of the target.

In still another embodiment, the present invention relates to a multi-energy polarization imaging system comprising: (A) at least one light source for illuminating a target with at least one quantity of light, the at least one quantity of light comprising at least two wavelengths of light, a first wavelength and a second wavelength, the second wavelength being different than the first wavelength; (B) a polarization-state generator for generating a polarization state for each quantity of light, the polarization-state generator comprising at least one polarizer, each polarizer being adapted to polarize an individual wavelength before the one or more quantities of light enter through at least one rotating ¼ waveplate linear retarder; (C) a polarization-state receiver for evaluating a resulting polarization state of each of the one or more quantities of light following illumination of the target, the polarization-state receiver comprising at least one second rotating ¼ waveplate linear retarder through which the one or more wavelengths of light are transmitted before entering at least one second polarizer; (D) an image-capture device for capturing at least a first image and a second image of the target illuminated by the at least one quantity of light, the first image corresponding to an image of the target generated from the first wavelength of light and the second image corresponding to an image of the target generated from the second wavelength of light, wherein the image-capture device receives and/or generates for each of the at least first and second images at least 16 individual polarization-state measurements; and (E) a processing unit for comparing the at least 16 individual polarization state measurements from the at least first and second images.

In still another embodiment, the present invention relates to a method for generating a multi-modality image of a target, the method comprising the steps of: (i) emitting at least two quantities of energy, at least one quantity of energy being a quantity of light having a first wavelength, the second quantity of energy having a second wavelength different from the first wavelength, the second wavelength being selected from the gamma ray, X-ray, ultraviolet ray, visible, infrared ray, radar, RF, microwaves, and/or radio wave portions of the electromagnetic spectrum; (ii) creating an initial polarization state for at least the one quantity of light by polarizing and then retarding one component of the one quantity of light relative to another component of the at least one quantity of light; (iii) directing the at least two quantities of energy generally toward the target so that the target is irradiated by the at least two quantities of energy, including directing the polarization state of any polarized energy generally toward the target in the instance where at least a portion of the energy is polarized; (iv) analyzing a resulting polarization state for each of the first and second quantities of energy by retarding one component of the first and second quantities of energy following irradiation of the target relative to another component of the first and second quantities of energy, and then polarizing the retarded first and second quantities of energy; (v) capturing a first image of the target irradiated by the first quantity of energy and a second image of the target irradiated by the second quantity of energy; (vi) optionally weighting at least one of the first and second images; and (vii) generating the multi-energy image of the target by evaluating a weighted difference between the first and second images, and/or by comparing and/or combining the first and second images.

BRIEF DESCRIPTION OF THE FIGURES

The foregoing and other features and advantages of the present invention will become apparent to those skilled in the art to which the present invention relates upon reading the following description with reference to the accompanying drawings, in which.

DETAILED DESCRIPTION

Figure 1:
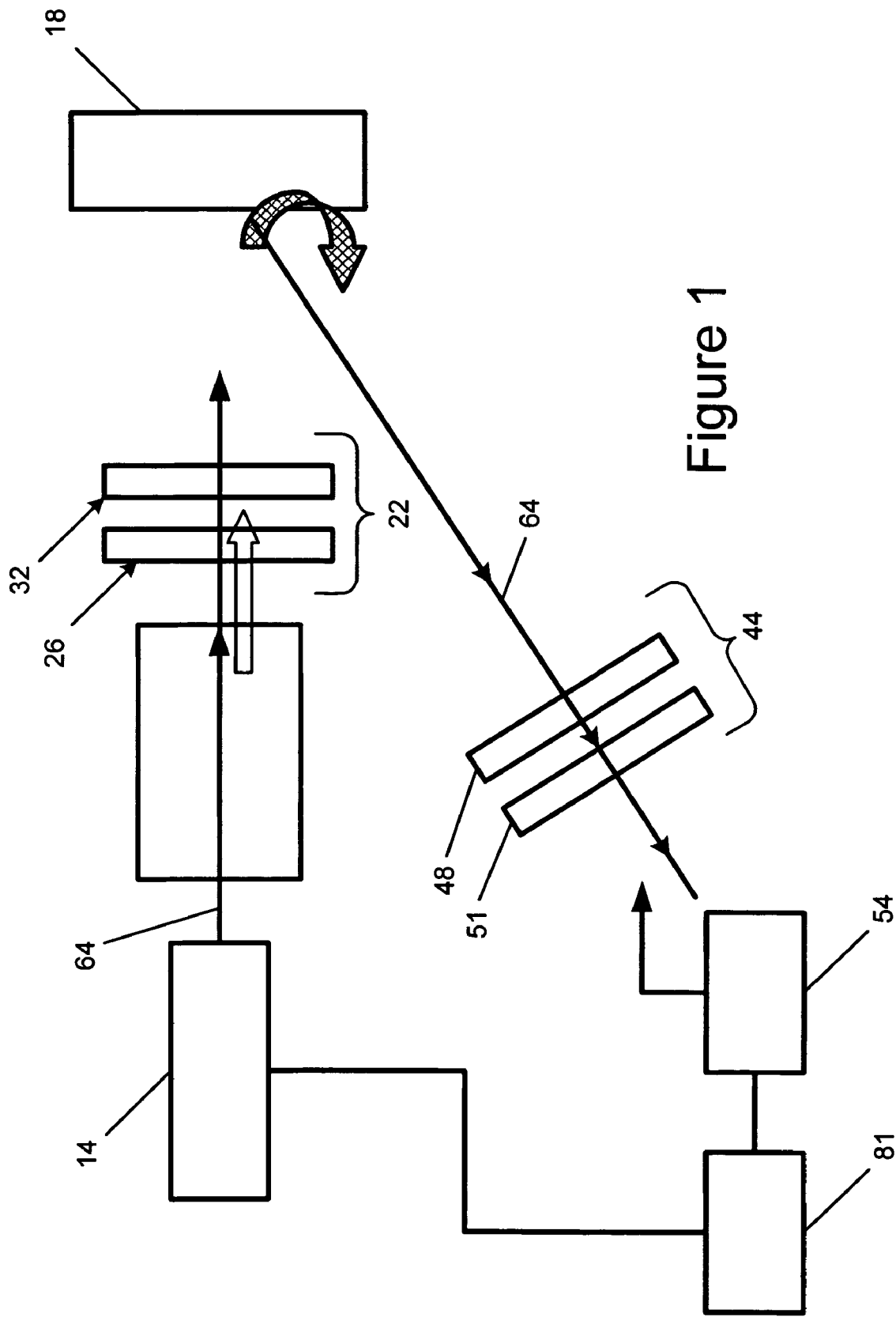
FIG. 1 is a schematic representation of a multi-spectral, multi-fusion, dual-energy Mueller-based optical imaging system in accordance with the present invention configured in a backscattered mode.

This invention is referred interchangeably through out the invention as "Mueller Matrix/Stokes Parameters Polarimetric Spectral Difference Imaging" or "Mueller Matrix/Stokes Parameters Polarimetric Dual-Energy Imaging", without loss of meaning, since it leads to the formation of several Mueller matrix polarimetric difference images and/or Stokes polarization Parameters image differences, formed by pairs of Mueller matrix polarimetric images/Stokes polarization Parameters images, acquired at at least two distinct wavelengths, chosen from a wavelength spectrum $\lambda_1, \ldots \lambda_n$. Therefore, multiple spectral polarimetric image differences can be obtained.

The present invention relates to a multi-energy system that generates and/or forms images of targets/structures by applying Mueller matrix imaging principles and/or Stokes polarimetric parameter imaging principles to data obtained by the multi-energy system. In one embodiment, the present invention utilizes at least one energy or light source to generate two or more Mueller matrix and/or Stokes polarization parameters images of a target/structure, and evaluates the Mueller matrix/Stokes polarization parameters multi-spectral difference(s) between the two or more images of the target/structure. As a result, high contrast, high specificity images can be obtained. Additional information can be obtained by and/or from the present invention through the application of image, Mueller matrix decomposition, and/or image reconstruction techniques that operate directly on the Mueller matrix and/or Stokes polarization parameters.

The present invention also relates to optical imaging techniques for efficient detection, characterization, and/or interrogation of targets/samples. High-contrast multi-spectral Mueller matrix/Stokes parameters polarimetric difference images, and the like can be obtained from targets embedded in turbid or cluttered, or low-contrast/low-detectability media. Besides homeland security and defense applications the present invention can play an important role in medicine and biology assisting in the early diagnosis, treatment, assessment, and follow-up of cancer (e.g., melanoma), image-guided biopsy, ophthalmology, molecular imaging, drug production and delivery, physiological imaging, nanotechnology, space exploration, robotic vision and inspection and repair of spacecraft; and inspection, characterization, classification, and monitoring of MEMS, nanostructures, wafers and masks for the microelectronic industry.

The principles of multi-spectral Mueller matrix-polarimetric image difference of this invention comprise multiple optical Mueller polarimetric images, obtained at different wavelengths. A weighted subtraction of any high-energy Mueller matrix image (low wavelength) image from a low energy (high wavelength) Mueller matrix image produces a polarimetric Mueller matrix image difference. Further imaging information of the target/sample/structure can be obtained by applying Mueller matrix polar decomposition of images obtained at at least two different wavelengths, thereby yielding image differences between at least one set of images obtained from a target/sample/structure at at least two individual wavelengths. In fact, Mueller matrix measurement allows parameters such as diattenuation, retardance, depolarization power, and birefringence to be obtained. The importance of these parameters can be enhanced further under multi-spectral interrogation of the target, providing useful information regarding the nature of the target.

For instance, interrogation of biological structures with multiple wavelengths, leads in practice to a multilayer interrogation of tissue, allowing one to obtain high-contrast images at different depths. This permits/allows one to differentiate tumor and cancerous structures or cells from healthy ones based on a change in tissue birefringence. Therefore, a subtraction of the birefringence obtained at at least two distinct wavelengths can enhance the structure of interest, removing the interfering tissue or cells. Therefore subtraction of the diattenuation, retardance, depolarization power, and birefringence at distinct wavelengths, under multi-spectral interrogation of a target can provide insightful structural and physiological information based on the difference of the attenuation of amplitude of incident light, phase change difference, depolarizing potential of the target difference, and/or phase shift difference, due to the variation of index of refraction, obtained at least two distinct wavelengths, respectively. Therefore, multi-spectral interrogation of the target, and formation of Mueller matrix-polarimetric image differences, can enhance just a specific region of interest (ROI) of the target over another ROI.

Further image enhancement can be achieved, by means of Stokes parameters formalism, by forming polarimetric images differences, and the like such as degree of polarization (DOP) difference, degree of linear polarization (DOLP) difference, degree of circular polarization (DOCP) difference, obtained at different wavelengths. This methodology can increase by n-fold the signal-to noise ratio of the imaging targets.

The present invention can utilize a laser beam, or other light source or sources, in conjunction with suitable optical filters and components, to illuminate targets, samples, structures and/or scenes at specific wavelengths and interrogate their respective reflectance spectral features. The dual-phase rotating retarder polarimeter yields a complete measurement of all sixteen Mueller matrix elements. As a result, complete polarimetric signatures of the targets are obtained. The acquisition of Mueller-matrix/Stokes parameters polarimetric optical images, one produced from a high energy (small wavelength) and another from a low energy (large wavelength) laser beams, and the subsequent subtraction of these two images, can produce high-contrast polarimetric image difference which eliminates or minimizes interfering background and clutters, or enhances the image process, meanwhile provide, spectral, energy, polarization-based amplitude contrast and phase contrast information, enhanced ROI's, enhanced contrast, enhanced specificity, and high signal-to-noise-ratio. The detected signal can be further enhanced by embedding fluorescent particles or molecules, quantum dots, nanostructures, dopants, polar molecules, chemo luminescence and bioluminescence particles or molecules, into the target/background.

The present invention operates on multi-spectral, multi-fusion, multifunctional, Muller Matrix polarimetric principles. It is capable of interrogating targets or samples with multiple wavelengths forming multi-spectral Mueller matrix multi-wavelength polarimetric difference images. Multi-spectral target interrogation gives rise to multi-wavelength Muller matrix polarimetric image differences obtained at different wavelengths, which also contain energy, spectral, polarization-based amplitude contrast and phase contrast information simultaneously. These principles apply not only to the interrogation of multiple targets but also single targets as well, giving rise to enhanced spectral and polarimetric contrast data.

FIG. 1 illustrates one embodiment of a multi-energy polarization imaging system 10 according to the present invention. The system of the present invention can be operated as a Mueller matrix polarimeter or as a Stokes parameter polarimeter depending upon the choice and operation of the components contained therein. The imaging system 10 includes a light source 14 (e.g., a multi-spectral light source) for illuminating a target 18 with a first quantity of light having at least a first wavelength and a second wavelength of light. Alternatively, the present invention can utilize a light source 14 for illuminating a target 18 with a first quantity of light having at least a first wavelength and a second quantity of light having a second wavelength. However, the present invention is not limited to just the above embodiments. Rather, the present invention can utilize one or more quantities of light, each quantity of light being composed of at least one specific wavelength of light and/or energy, or even two or more specific wavelengths of light-and/or energy.

A polarization-state generator 22 is provided for generating a polarization 22 state for each of the first and second wavelengths of light. The polarization-state generator includes a first polarizer 26 through which the first and second wavelengths of light are transmitted before entering a first waveplate 32 (e.g., a one-quarter waveplate), which creates a phase difference between an ordinary component 36 (FIG. 3) and an extraordinary component 42 (FIG. 3) of the polarized first and second wavelengths of light. A polarization-state receiver 44 is positioned to evaluate a resulting polarization state of the first and second wavelengths of light following illumination of the target 18, the polarization-state receiver 44 including a second waveplate 48 (e.g., a one-quarter waveplate) through which the first and second wavelengths of light are transmitted before entering a second polarizer 51. The polarization-state receiver can be just a receiver or it can be both a receiver and a polarization-state analyzer, if so desired.

An optical image-capture device, such as a charge-coupled device ("CCD"), photo-electronic camera, CMOS detector, and the like, captures a first image of the target illuminated by the first wavelength of light and a second image of the target illuminated by the second wavelength of light. A processing unit 57 assigns a weighting factor to at least one of the first and second images and evaluates a weighted difference between the first and second images to generate a multi-energy image (or polarimetric image) of the target 18. For instance, where both waveplates are one-quarter retarders and whether both one-quarter retarders rotate, or just the second one-quarter retarder rotates, under suitable orientation of the optical components, the system of the present invention forms a Dual-Phase Rotating Retarder complete Mueller Matrix Polarimeter, or a Rotating Retarder Stokes Parameters polarimeter. Therefore, enhanced Mueller matrix spectral image differences and Stokes parameters spectral image differences can be obtained, respectively.

Figure 4:
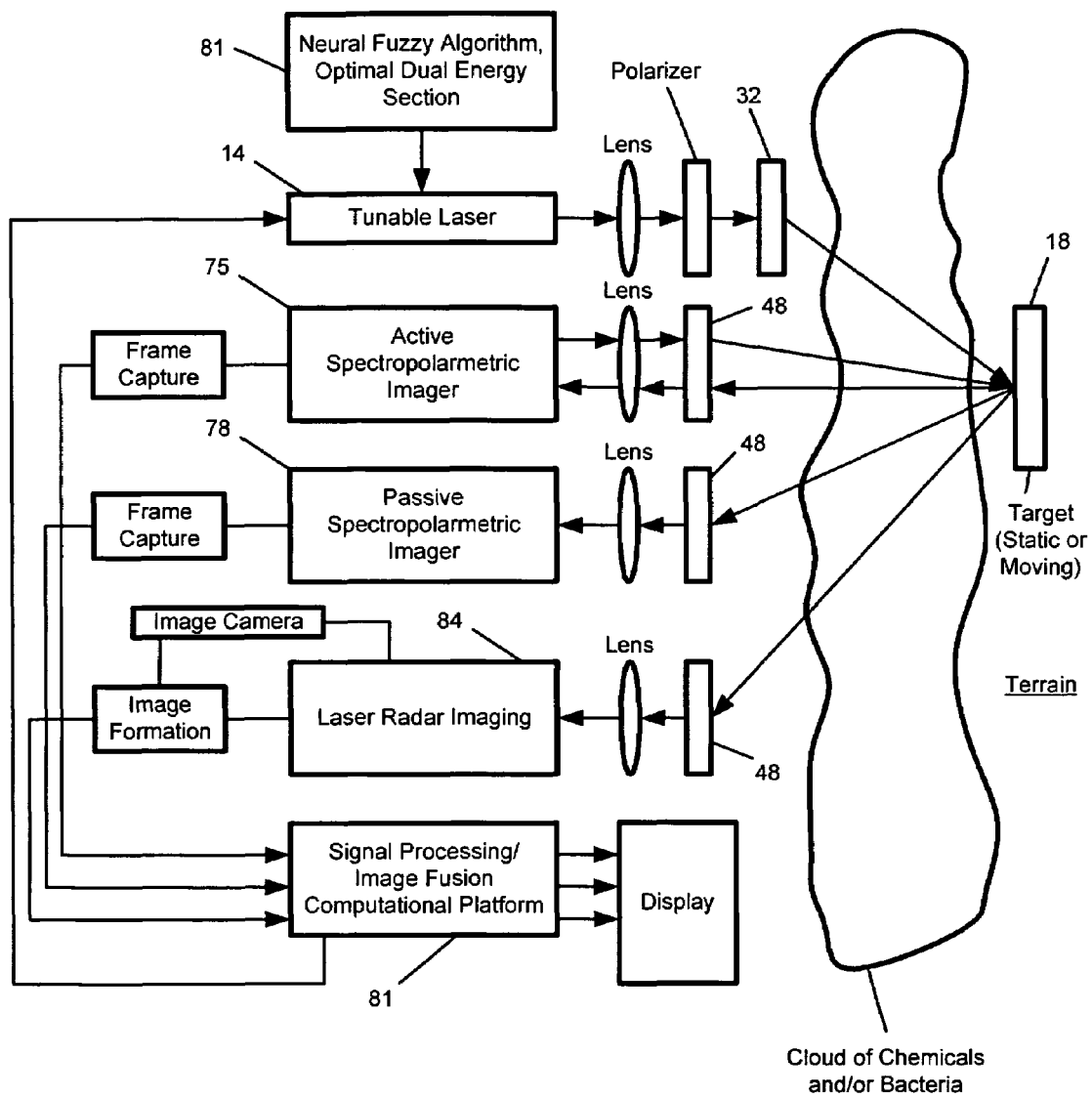
FIG. 4 is a block diagram of a multi-spectral, multi-fusion, dual-energy Mueller-based optical imaging system in accordance with the present invention implemented with an active multi-spectral spectro-polarimeter, a passive multi-spectral spectro-polarimeter, and a laser radar system.

Alternatively, or in addition to, the processing unit 57 can process at least 16 individual polarization-state measurements received/derived from the images generated from the first and second wavelengths of light. These values, can be averaged together to form average polarimetric images at distinct wavelengths. Then, the first average polarimetric image corresponding to an image of the target generated from the first wavelength of light and the second average polarimetric image corresponding to an image of the target generated from the second wavelength of light, are subtracted to each other so that to obtain a weighted spectral image difference of the target. Alternatively, or in addition to, the processing unit 57 can process at least 16 individual polarization-state measurements This will maximize the signal-to noise ratio of the target images. The imaging system 10 of the present invention can be combined with an active or passive multi-spectral spectropolarimeter 75, 78 (FIG. 4) or multi-spectral/hyperspectral imaging system for enhanced imaging, as well as with laser sources, white light sources, partially polarized sources, multiple exposures, and the like. As a result, a multi-wavelength, multi-fusion optical imaging system 10 with enhanced contrast and specificity can be obtained. In addition, the system 10 can be operated as a polarimeter laser reflectometer, or as a network of several polarimeters (FIG. 5) operating in reflection or transmission mode, or any combination of these modes. It can also be implemented with super-resolution techniques (variable focus lenses, or algorithms), as well provide imaging information at variable depths (axial direction along a focal axis in which the light propagates), either by translating the target along the focal-axis, via a computerized translational motorized stage, or utilizing standard confocal microscopy techniques. As a result, multi-spectral polarized multi-wavelength planar image sections, at the longitudinal directions can be obtained.

One advantage of the present invention is that the multi-spectral polarimetric principles can lead to the design of novel high contrast confocal microscopes. Instead of using moving lenses to scan the focal spot in the axial and radial dimensions, one can obtain longitudinal planes of the sample, through multi-wavelength polarimetric interrogation of the target, without scanning the focal spot at the axial direction. In fact, this leads to different imaging depths of the target, due to the different absorption and scattering characteristics of each optical wavelength within the sample. Combining Mueller matrix/Stokes parameters spectral image differences, enhanced slices of information within the tissue, with high background rejection can be obtained. These concepts apply to both transmission, reflectance and fluorescence confocal microscopes. This technique minimizes the use of a focused lens, improving therefore, the x-y resolution, and increasing depth of imaging.

In yet another embodiment, the present invention can be utilized to develop multi-spectral polarimetric optical computed tomography CT systems. Interrogation of targets with multi-spectral polarized optical wavelengths and exploitation of the Mueller matrix/Stokes parameters spectral image differences could lead to the development of optical CT systems with dual-energy tomographic capabilities. Therefore, enhanced signal-to-noise ratio, high-contrast high background to signal rejection ratio, and images with significant metabolic and physiological information would be obtained. This technology would complement PET and SPECT, fMRI, MEG, and EEG, and x-ray CT.

In still another embodiment, the imaging system 10 of the present invention fuses dual-energy imaging principles with polarimetric imaging principles, optionally at varying focal depths and exposures, to generate and display a high-contrast image. The interrogation of a target 10 with two or more quantities of light having different wavelengths (multi-spectral interrogation), and the acquisition of polarimetric images by applying dual-rotating quarter-wave linear-retarder complete-polarimeter techniques, allows one to obtain enhanced polarimetric signatures by subtraction of the polarization parameters of the acquired images, such as degree of polarization (DOP), degree of linear polarization (DOLP), degree of circular polarization (DOCP), ellipticity, azimuth, and eccentricity, or their differences such as DOP difference, DOLP, difference, DOCP difference, obtained at different wavelengths Although described herein as a dual-energy imaging system, it should be understood that the system 10 of the present invention can be used to generate and display any multi-energy image. Instead of being limited to two quantities of light, a plurality of light quantities, described interchangeably herein as beams of light, laser light beams, and laser beams, each having a different wavelength, are used to illuminate and/or irradiate the target 18 for capturing images of the target 18. Alternatively, the present invention can also utilize at least one quantity of light, where the light quantity simultaneously or discretely contains therein at least two different wavelengths of light. In still another embodiment, the present invention can utilize at least one quantity of light, where the quantity of light contains at least one wavelength of visible light, in conjunction with one or more additional energy sources that is/are capable of generating at least one wavelength of energy from the gamma ray, X-ray (both very soft X-rays and X-rays), ultraviolet ray, infrared ray, radar, RF, microwave, and/or radio wave portions of the electromagnetic spectrum. Instead of, or in addition to, the present invention can also utilize an energy source capable of generating one or more wavelengths of acoustic and/or ultrasound energy in conjunction with at-least one wavelength of visible light.

Thus, the present invention is designed to form difference images from two Mueller matrix images/Stokes parameters images acquired at very different wavelengths. For instance, a first wavelength may be in the visible region of the spectrum, forming a Mueller matrix polarimetric image, while a second may be in the gamma ray, X-ray (both very soft X-rays and X-rays), ultraviolet ray, infrared ray, radar, and/or radio wave portion of the electromagnetic spectrum (or even an acoustic and/or ultrasound wavelength), as is discussed above.

Regardless of the number of different wavelengths used for illumination purposes, the principles of multiple-energy imaging involve the use of two or more images to generate a multi-energy image. In a two wavelength embodiment of the present invention, a first image is captured by illuminating the target 18 with light having the first wavelength, and at least one more image is captured by illuminating the target 18 with light or some other energy source having a second wavelength that is different than the first wavelength. Optionally, this can be performed with a quantity of light having a first wavelength and another quantity of energy or light having a second wavelength that is either longer or shorter than the wavelength of the light.

The terms long and short as used with reference to the wavelengths of light and/or energy used to illuminate/irradiate target 18 are relative terms that are ordinarily open to subjective interpretation. As used herein, however, the terms long and short are relative to common electromagnetic spectrum known to those of skill in the art.

In the embodiment depicted in FIG. 1, a weighted subtraction of the two images produces a multi-energy image which minimizes interfering background structures. A weighting factor is assigned to at least one polarization parameter of one or more of the captured images such that the desired contrast is achieved in the multi-energy image generated by evaluating a difference between the images of the target 18 illuminated with the quantities of light having different wavelengths. By weighting at least one of the polarization parameters of an image of the target illuminated at a given wavelength, a suitable amount of undesired interfering objects possibly obstructing the target 18 can be removed from the multi-energy image. For instance, the target 18 and its ambient environment or background can exhibit poor optical contrast due to similar reflectance properties for light at a first wavelength, while the background is the dominant reflective entity at a second wavelength. Capturing a first image of the target 18 and background illuminated by light having the first wavelength and a second image of the target 18 and background illuminated by light having the second wavelength, and then subtracting the background-dominant second image from the first image results in a high contrast multi-energy image of the target 18.

Multi-energy images of the present invention can be one dimensional, two dimensional, and three dimensional. Further, the optical image-capture device 54 can rely on homodyne, heterodyne, superheterodyne detection principles, image intensifiers, photomultipliers, semiconductor detectors, including but not limited to the use of auto balanced detectors and lock-in amplifiers.

Examples of the polarization parameters of the captured images that can be weighted for subtraction from the corresponding polarization parameters of another image captured by illuminating the target 18 at a different wavelength include, but are not limited to: degree of polarization ("DOP"), degree of linear polarization ("DOLP"), degree of circular polarization ("DOCP"), ellipticity, azimuth, and eccentricity. The weighted subtraction can also be performed using sets of images, in which case the subtraction will performed on the differences of the sets such as DOP difference, DOLP difference, DOCP difference, ellipticity difference, azimuth difference, eccentricity difference and the like.

Further enhancement is obtained, when warranted, by employing applied polarimetric techniques, and optionally, by also employing focal-length scanning of the object. Focal-length scanning of the target 18 is obtained by varying the focal depth of a lens positioned in front of the target 18 to focus the light so that it converges at a suitable depth within the target 18. This illuminates a single "slice" of the target 18 located a predetermined distance from the lens in the axial direction in which the light propagates. The process is continuously repeated for several different focal depths until the desired portion of the three-dimensional target 18 has been captured as an image.

Figure 2:
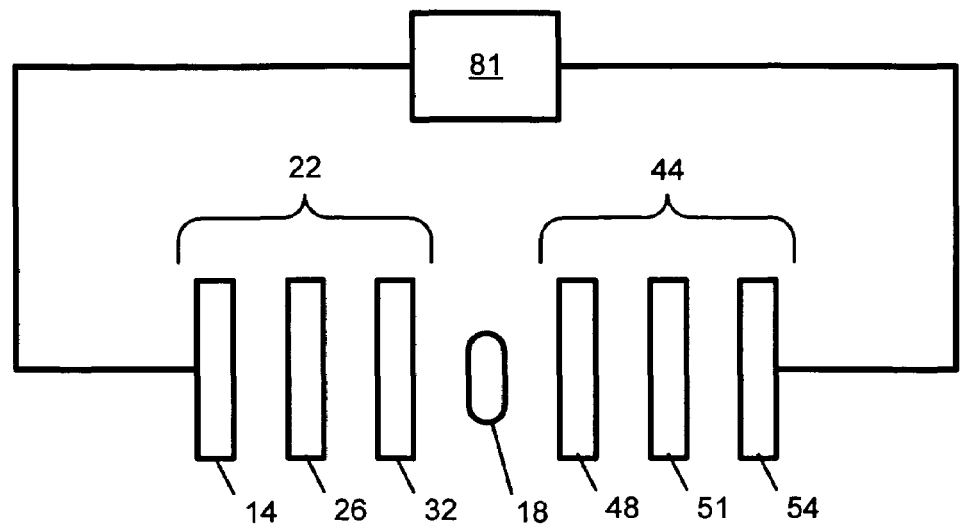
FIG. 2 is a schematic representation of a multi-spectral, multi-fusion, dual-energy Mueller-based optical imaging system in accordance with the present invention configured in a transmission mode.

A one-quarter rotating retarder is positioned adjacent to respective polarizers to form a polarization-state generator 11 and a polarization-state receiver 44 for generating and analyzing, respectively, the polarization state of the first and second quantities of light. The polarization-state generator 22 and receiver 44 operate in conjunction with dual-energy imaging techniques described above. It can be configured to operate in a transmission mode, as shown in FIG. 2, and a backscattered mode as shown in FIG. 1. The adaptability of the present invention allows it to be used in a variety of applications including, but not limited to, medical, aerospace and industrial. For example, the imaging system 10 of the present invention can be used in adverse atmospheric conditions for both air-to-ground and ground-to-ground combat applications. Additionally, the imaging system 10 can be adapted for use in diagnosing medical disease by generating enhanced images of the internal cavity of a patient.

Figure 3:
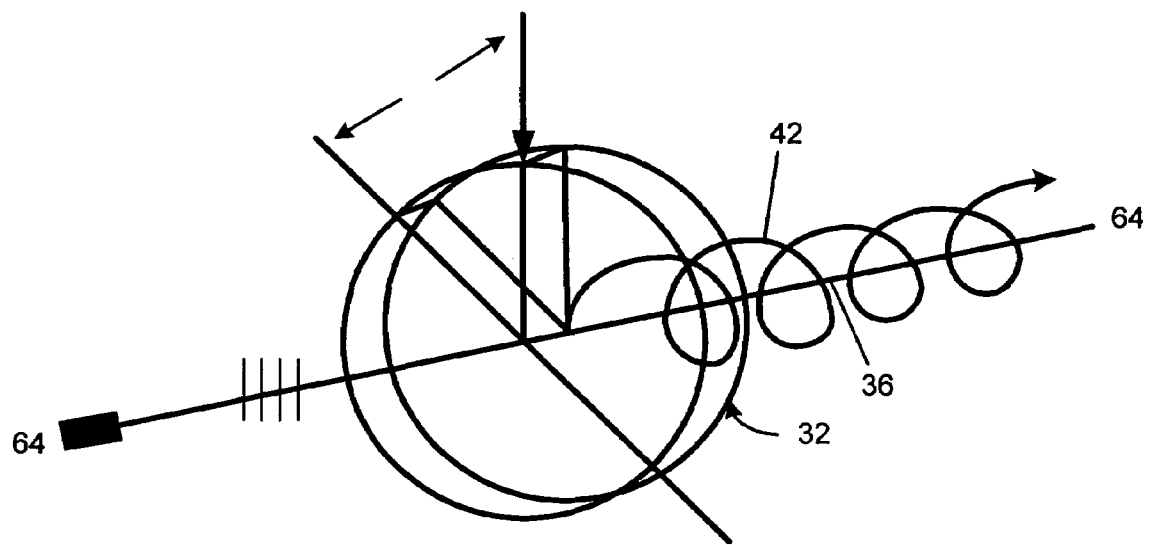
FIG. 3 is a schematic illustration of a quarter-wave retarder in accordance with the present invention.

An exemplary configuration a one-quarter waveplate forming a portion of the polarization-state generator 22 and the polarization-state receiver 44 in the present system is shown in FIG. 3. Polarization states are generated by placing the polarization-state generator 22 in optical alignment along the optical axis 64. Arranged in this manner, the light source 14 emits light that is polarized by the first polarizer 26 and subsequently transmitted through a first waveplate 32. The polarization state of light transmitted from the first waveplate 32 is then analyzed by the polarization-state receiver 44 after the light transmitted from the first waveplate 32 has illuminated the target 18.

Similar to the polarization-state generator 22, the polarization-state receiver 44 includes a second waveplate 48 and a second polarizer 51. Unlike the polarization-state generator 22, however, the polarization-state receiver 44 is arranged such that light illuminating the target is transmitted through the second waveplate 48 prior to being received by the second polarizer.

The first and second waveplates 32, 48 in one embodiment are rotatably supported between the first and second polarizers 26, 51 along the optical path 64 traveled by the light from the light source 14. Rotating the second waveplate 48 at an angular-velocity ratio of 5:1, or even at an angular velocity of 5:1 or less, relative to the first waveplate 32 encodes the 16 parameters of the target's Mueller matrix, which is discussed in detail below, onto the Fourier components of the detected signal. Further, the first and second waveplates 32, 48 are positioned on opposite sides of the target 18, which means that the light used to illuminate the target 18 interacts with the target 18 between interactions with the first and second waveplates 32, 48. This does not require the first and second waveplates 32, 48 to be linearly aligned, but merely positioned along the optical path 64 traveled by the light from the light source 14 to the optical image-capture device 54. Thus, the system 10 can be arranged in a linear arrangement as shown in FIG. 2, or a backscattering mode as shown in FIG. 1.

The waveplates 32, 48 of the present invention, also known as retardation plates and phase shifters, are made from materials which exhibit birefringence. The velocities of ordinary and extraordinary light rays 36, 42 through the birefringent materials vary inversely with their refractive indices. The phrase "ordinary ray" is commonly used to refer to the component of the light incident on the waveplate 32, 48 that travels quickly through the waveplate material relative to the "extraordinary ray," 42 which travels through the waveplate material relatively slower than the ordinary ray 36. The difference in velocities through the waveplate material gives rise to a phase difference, also referred to as a phase shift, between the ordinary and extraordinary rays 36, 42. The degree of the phase difference introduced by the waveplates 32, 48 is dependent upon the path length through the waveplates 32, 48, which, in the present case, is equal to the thickness of the waveplates 32, 48. Waveplates 32, 48 that introduce a phase shift of between 0 and 90° between the ordinary and extraordinary light components 36, 42 produce elliptically polarized light (i.e., the ordinary and extraordinary components 36, 42 are not equal in length), while a phase shift of exactly 90° produces circularly polarized light where the ordinary and extraordinary components are equal in length. As mentioned above, elliptically and circularly polarized light tend to maintain their polarization more than linearly polarized light through many light-scattering media. According to one embodiment of the present invention, the first and second waveplates 32, 48 are sized to introduce a 90° phase shift between the ordinary and extraordinary 36, 42 components of the incident light. Since such a phase shift amounts to one fourth of a complete wave, waveplates 32, 48 of this size are referred to as quarter-wave retarders.

The first and second polarizers 26, 51 are fixed in position, and can be any material that impedes the transmittance of at least one component of light through the polarizer while allowing another component to pass therethrough generally unimpeded. By fixing the position of the first and second polarizers 26, 51, the effect of any instrumental polarization preceding or following the polarizers 26, 51 is minimized. Also, the Fourier transform on the data automatically performs a least squares fit to the undetermined data set. The present system 10 is also resistant to beam wander if measurements are made over a $2\pi$ cycle.

The light source 14 of the present invention can be any suitable device that can emit light energy. According to an embodiment of the present invention, the light source 14 is a tunable laser having a variably adjustable wavelength. By tunable, it is meant that the laser can be tuned to emit laser light having any wavelength within a predetermined range of wavelengths. Other suitable light sources 14 include, but are not limited to, hyperspectral/multi-spectral light sources, white light, partially polarized light sources, and the like. The multi-spectral, multi-fusion, dual-energy Mueller-based polarimeter system 10 of the present invention can also utilize short-duration optical pulses or snapshots of light pulses providing therefore, temporal information, in addition to the spatial and spectral information of the target 18. In another embodiment, reference numeral 14 can be an energy source that is able to emit at least one quantity of light having a wavelength in the visible spectrum and at least one quantity of energy having a wavelength that is longer or shorter than the wavelength of the visible light.

Further, the system 10 of the present invention can include a plurality of light sources 14 for illuminating the target 18. The plurality of light sources 14 can each illuminate the target 18 with a quantity of light having a different wavelength, forming an illumination plane or point on the target. By varying one or more of the geometry and the orientation of the light sources 14, a new plane or point of illumination on the target 18 can be established. This variation of the geometry and/or the orientation of the light sources can be repeatedly performed to generate a desired multi-energy image.

Using the present invention for applications such as designing optical tomography systems, for example, the light source 14 can be configured to utilize planar geometry, fan-beam geometry, pointwise illumination, or any combination thereof. Pointwise illumination should be provided by any beam steering mirror-like devices such as electromechanical, opto-electronic, acousto-optic, all optical-based technology, liquid-crystal-based mirror, and any other such devices.

Figure 5:
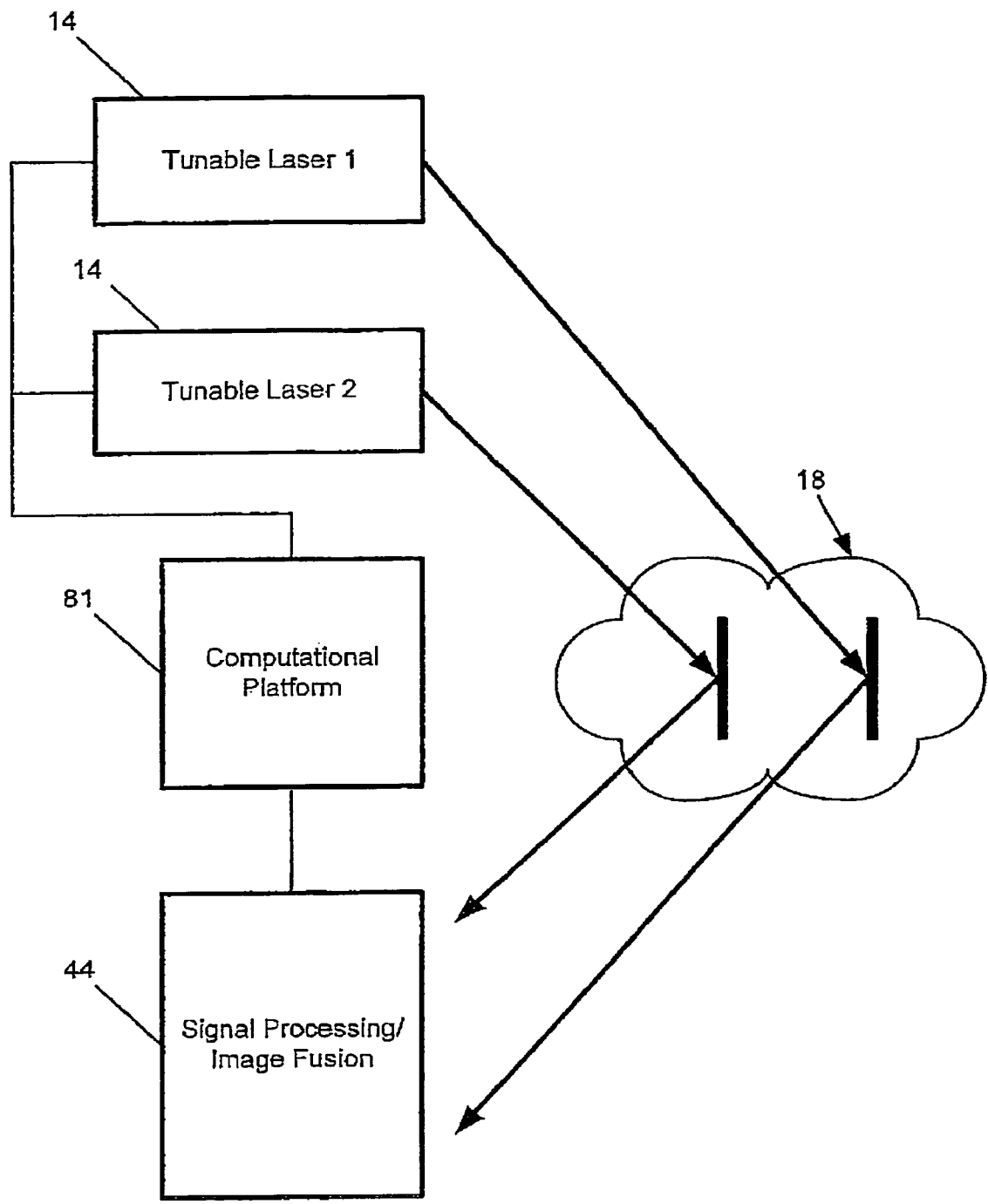
FIG. 5 is an illustrative arrangement of a network of multi-spectral, multi-fusion, dual-energy Mueller-based optical imaging systems in accordance with the present invention.

Additionally, an embodiment of the present invention shown in FIG. 5 implements a network comprising a plurality of dual-rotating-retarder complete Mueller-matrix polarimeters, each targeting a different location of the target 18. This embodiment can be implemented by positioning a dual-phase rotating-retarder complete Mueller-matrix polarimeter imaging system 10 of the present invention at a plurality of locations relative to the target 18. Similar to the individual imaging system 10, each imaging system 10 in the network illuminates the target 18 with two or more quantities of light, each quantity of light having a different wavelength. However, unlike the individual imaging system 10, each imaging system 10 in the network focuses the first and second quantities of light to penetrate the target 18 at different depths or on different surface areas. The weighted subtraction of polarization parameters acquired by illuminating the target 18 with the quantities of light having different wavelengths is performed for each individual imaging system 10 in the network to generate individual multi-energy polarimetric images. Each of these individual images is then communicated to a common computational platform 81 where a composite image of the target 18 is generated from a combination of the individual images. As the network is illustrated in FIG. 5, the polarization-state generator 22 and light source 14 of each individual imaging system 10 are represented generally by the blocks entitled "TUNABLE LASER 1" and "TUNABLE LASER 2". Similarly, the polarization-state receiver and optical-imaging device for each imaging system 10 in the network is represented generally as the block entitled "SIGNAL PROCESSING/IMAGE FUSION." The composite image can be a three-dimensional image of the target 18, a two-dimensional image of the target's surface, or any other type of image. Furthermore, the composite image can be formed by subtracting an individual image of a layer within the target 18 from another individual image of a different layer within the target 18. In this manner, interference from one layer of the target 18 that could obstruct the view of the layer of interest in the target 18 in the composite image is minimized.

The common computational platform 81 can store information concerning the wavelengths of the light emitted by each individual imaging system 10 in a database stored in a computer readable memory for optimizing operation of the network in future applications. An artificial neural network ("ANN"), described in detail below, can be used with the computational platform 81 to select optimal wavelengths for the individual light sources 14 of the network. The optimal wavelengths can depend on a variety of factors such as atmospheric conditions through which the quantities of light are to be transmitted, properties of the target 18 (i.e., whether the target region of interest includes biological tissue, bone structures, gaseous elements, hardened structures, synthetic objects, radioactive materials, etc.), and other factors. Further, similar to the individual imaging systems 10, one or more of the individual imaging systems 10 of the network can be in a fixed position, dynamically positioned in an aircraft, satellite, medical instrumentation, and the like, and include applications for target surveillance and identification, homeland security, air defense, battleship awareness,;and other suitable applications. Likewise, the target 18 can be static or dynamic. And again, referring to FIG. 4, the individual imaging systems 10 and the network can be implemented with an active spectro-polarimetric imager 75, passive spectro-polarimetric imager 78, laser radar imager 84, and any combination thereof.

The necessary computational hardware and software for the operation of the system 10 of the present invention is in operational communication with the features of the system 10 discussed above. The computational platform includes at least a processing unit operatively connected to a computer readable memory. Computer logic stored in the computer-readable memory along with information collected from previous operations of the system 10 and pre-programmed into the computer readable memory allow the system 10 to adaptively select suitable wavelengths for the first and second quantities of light based on at least the ambient environment of the target 18. For example, the computational platform can include what is commonly referred to as an intelligent system, such as an artificial neural network, to determine the optimal wavelengths to be used for target recognition and identification. This can be used to search for targets 18 amidst camouflage nets, trees, fog or other adverse atmospheric conditions, to locate a known composition inside the body of patient in a medical context, and other similar applications.

Generally, an artificial neural network ("ANN") includes highly-interconnected simple computing mathematical nodes, analogous to neurons in a biological neural network. The interconnections between these mathematical nodes (neurons), resembling synapses in biological neural networks, are called weights and provide means to store knowledge. The functional mappings are acquired through a learning process and the knowledge is stored in the form of weights. The leaning process involves repeated training in order to accurately learn the task. Alternatively, a database of information can be preprogrammed into the computer-readable memory to minimize the time required for the learning process.

In one embodiment, the present invention utilizes an ANN of the present invention uses a committee of neural networks to increase the reliability of choices made by the ANN. Three or more ANNs are trained with different architecture, initial weights, and the best ANNs are recruited to form a committee for selecting the appropriate light wavelengths. Inexact-reasoning techniques such as fuzzy logic can be employed to further enhance the system.

Figure 6:
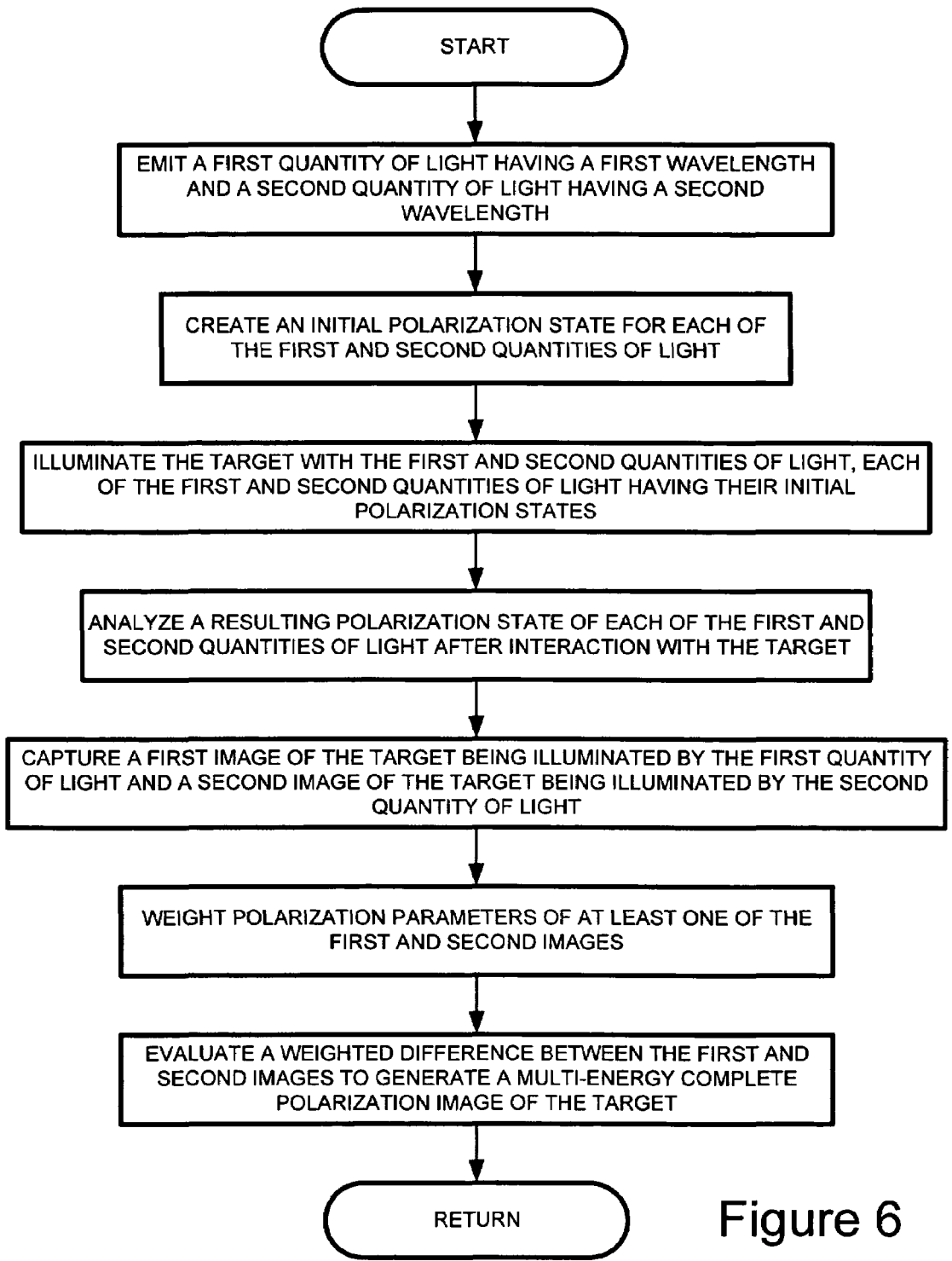
FIG. 6 is a flow diagram of an embodiment of a method for generating a multi-energy image in accordance with the present invention.

In use the system of FIG. 1 operates as follows, with reference to FIG. 6, the multi-spectral, multi-fusion, dual-energy Mueller-based polarimeter imaging system 10 of the present invention can generate enhanced multi-energy images according to a method of the illustrative embodiment. This illustrative method includes the steps of emitting a first quantity of light having a first wavelength 101 and a second quantity of light having a second wavelength that is different than the first wavelength, creating an initial polarization state for each of the first and second quantities of light by polarizing and then retarding one component of each of the first and second polarized quantities of light relative to another component of the first and second quantities of light 104, and directing the polarization state for each of the first and second quantities of light generally toward the target 107. The method of the illustrative embodiment further includes analyzing a resulting polarization state for each of the first and second quantities of light by retarding one component of the first and second quantities of light following illumination of the target 18 relative to another component of the first and second quantities of light 110, and then polarizing the retarded first and second quantities of light 110; capturing a first image of the target 18 illuminated by the first quantity of light and a second image of the target 18 illuminated by the second quantity of light 113; weighting at least one of the first and second images 116; and generating the multi-energy image of the target by evaluating a weighted difference between the first and second images 119. The weighting factor in some circumstances can be unity, or take on any other value.

The step of creating an initial polarization state 104 includes linearly polarizing the first and second quantities of light. After the linear polarization, at least one of the ordinary and extraordinary components 36, 42 of the linearly-polarized light is retarded with a quarter-wave retarder 32 to create a phase angle between the ordinary and extraordinary components 36, 42.

Similarly, analyzing the resulting polarization state 110 includes analyzing a resulting phase angle between the ordinary and extraordinary components 36, 42 of the first and second quantities of light following interaction of the first and second quantities of light with the target 18. This step evaluates the effect the target 18 has on the polarization state of the first and second quantities of light by transmitting the first and second quantities of light through a second quarter-wave retarder 48 following interaction with the target 18. Then, the first and second quantities of light are again linearly polarized by the second polarizer 51.

Weighting at least one of the first and second images includes 116 the steps of determining a Mueller matrix for each of the first and second images, determining a weighting factor suitable for at least one parameter of the first and second images, and multiplying at least one of the parameters of the first and second images by the value of the weighting factor.

Generating the multi-energy image of the target 119 includes the steps of determining a difference between the at least one weighted image parameter and the remaining image parameter, generating a Mueller matrix for the difference between the two images, and displaying an image generated from the Mueller matrix for the difference between the two images.

Emitting a first quantity of light having a first wavelength and a second quantity of light having a second wavelength 110 includes evaluating an ambient environment of the target 18, comparing the ambient environment of the target 18 to known conditions stored in a computer readable memory, and determining suitable first and second wavelengths based on the comparison between the evaluated ambient environment of the target 18 and the known environments in the computer readable memory using an artificial fuzzy neural network. The ambient environment can be any environment, neighboring object, and the like that can affect the first and second quantities of light en route to the target 18. Non-limiting examples of such an ambient environment include a gas cloud, fog, or other atmospheric condition through which the first and second quantities of light are transmitted between the light source 14 and the target 18 or other location along the optical path 54 from the light source to the optical image-capture device 54.

In another embodiment, the present invention is directed to efficient interrogation of targets surrounded by scattering media; detection of weak signals among cluttered targets; and identification, discrimination, and classification of targets; interrogation of a single target aimed to enhance specific ROI(s). The present invention can be operated in either a transmission or backscattering geometry.

Figure 7:
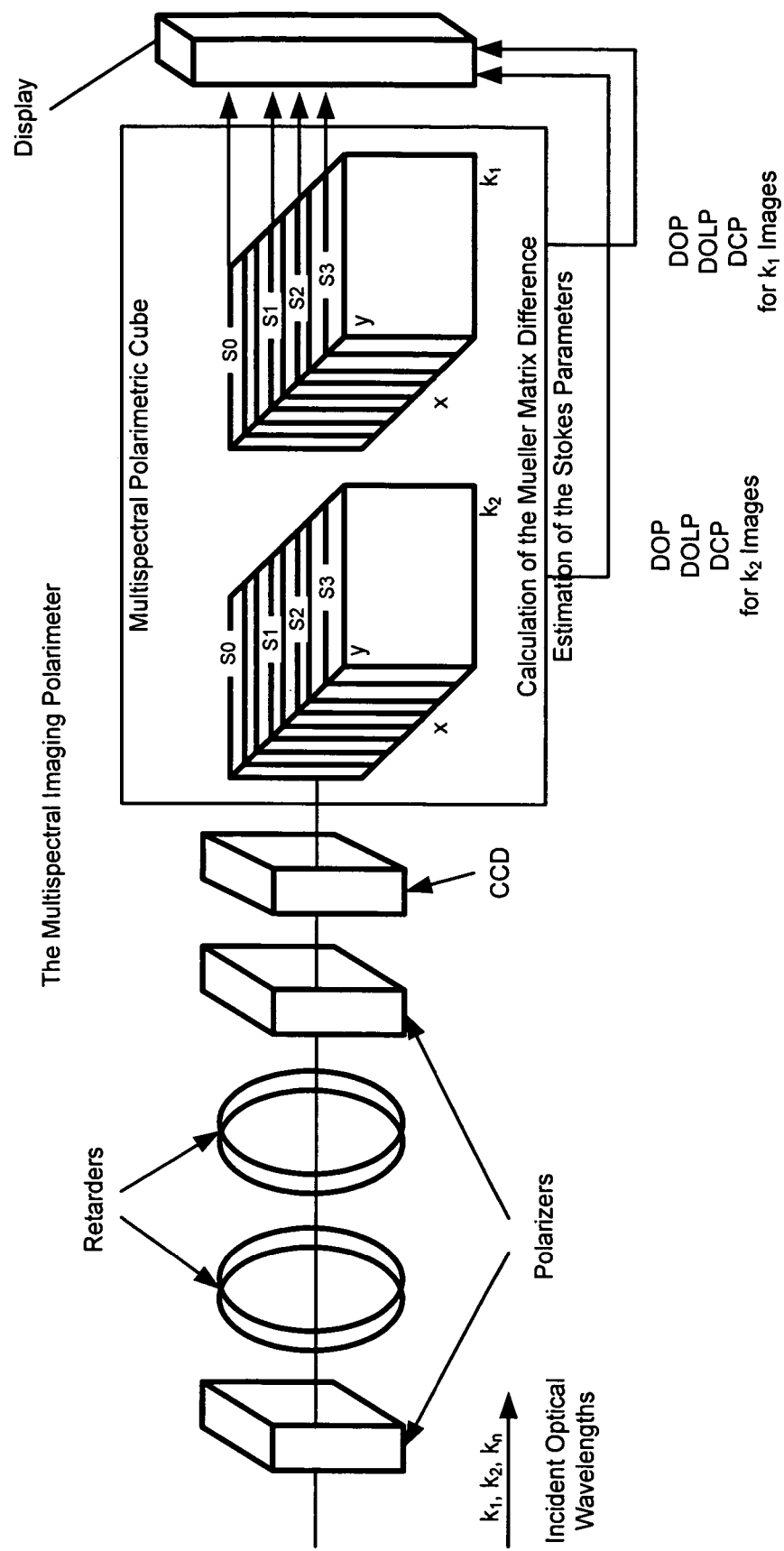
FIG. 7 is a diagram representing an example of a multi-spectral imaging polarimeter according to one embodiment of the present invention.

The principles of the multi-fusion multi-spectral-rotating retarder, dual-energy complete polarimeter, are shown in FIG. 7. The principles of spectral difference or dual-energy Mueller matrix polarimetric imaging on this contribution involve the use of a pair of optical Mueller polarimetric images, chosen from n Mueller matrix polarimetric image differences, interrogated by n optical wavelengths. A weighted subtraction of the sixteen matrix elements at different wavelengths, can produce polarimetric Mueller matrix image differences, which eliminates interfering background structure. Similarly, extending the above treatment, by means of Stokes polarization parameters, we can generate spectral Stokes polarimetric parameter differences.

As will become apparent in view of the discussion below, the data from both the multi-spectral imaging camera can be interpreted as an image of a four-dimensional multi-spectro-polarimetric volume because a measure of radiance is obtained for four independent variables or indices: two spatial variables (x, y), a wavenumber k (or a wavelength) and S which has only four possible values ($S_0$, $S_1$, $S_2$, $S_3$).

As noted above, the present invention is capable of performing multi-spectral Mueller matrix polarimetric difference imaging between optical wavelengths from all over the optical spectrum, as well as utilizing radiation from different portions of the electromagnetic spectrum such as combinations of visible, IR, radiofrequency (RF), microwave, milli-wave radiation, gamma and x-rays, ultrasound, MRI and the like.

The multi-spectral Mueller matrix polarimetric difference imaging principles can be fused with other signal modalities/descriptors such as frequency, phase, amplitude, temporal response, time range, 3D-imaging, time-ranging, interferometry, linear and nonlinear image analysis/processing algorithms, line spread function (LSF), Modulation Transfer Function (MTF), Fourier Transform, and others, leading to enhanced image performance and feature extraction.

The present invention can also form difference images from two Mueller matrix polarimetric images acquired at very different wavelengths. For instance, a first wavelength may be in the visible region of the spectrum, forming a Mueller matrix polarimetric image, while a second may be in the very soft X-ray, X-ray, gamma ray, both polarized or not, or even acoustic and ultrasound waves.

In some circumstances, it can also perform Mueller matrix polarimetric image subtraction between optical and/or electromagnetic polarimetric images, and diffracted soft x-rays or gamma rays polarized cases.

The present invention allows images at selected wavelengths to be acquired over a 180° or 360° phase retardation. Subsequent calculations are performed on each pixel of a target scene by measuring all four components of the Stokes vector simultaneously, from the 16 Mueller matrix elements, as a function of the incident wavelength. Although, 16 different polarization images can be obtained, 36 or 49 polarimetric measurements yield to improved images, due to error calibration reduction. In addition, polarimetric parameters such as degree of polarization (DOP), degree of linear polarization (DOLP), degree of circular polarization (DOCP), ellipticity, and orientation also can be calculated and provided in an image format.

The data from the muti-spectral imaging camera can be interpreted as an image of a four-dimensional multi-spectro-polarimetric volume because a measure of radiance is obtained for four independent variables or indices: two spatial variables (x, y), a wavenumber k (or a wavelength) and S, which has only four possible values ($S_0$, $S_1$, $S_2$, $S_3$).

Interrogation of the sample at multiple wavelengths yields several Mueller matrices, expressed as $$M_{(sample)\lambda 1,\lambda 2,\ldots,\lambda n} = \begin{pmatrix} m_{11\lambda_1,\lambda_2,\ldots,\lambda_n} & m_{12\lambda_1,\lambda_2,\ldots,\lambda_n} & m_{13\lambda_1,\lambda_2,\ldots,\lambda_n} & m_{14\lambda_1,\lambda_2,\ldots,\lambda_n} \\ m_{21\lambda_1,\lambda_2,\ldots,\lambda_n} & m_{22\lambda_1,\lambda_2,\ldots,\lambda_n} & m_{23\lambda_1,\lambda_2,\ldots,\lambda_n} & m_{24\lambda_1,\lambda_2,\ldots,\lambda_n} \\ m_{31\lambda_1,\lambda_2,\ldots,\lambda_n} & m_{32\lambda_1,\lambda_2,\ldots,\lambda_n} & m_{33\lambda_1,\lambda_2,\ldots,\lambda_n} & m_{34\lambda_1,\lambda_2,\ldots,\lambda_n} \\ m_{41\lambda_1,\lambda_2,\ldots,\lambda_n} & m_{42\lambda_1,\lambda_2,\ldots,\lambda_n} & m_{43\lambda_1,\lambda_2,\ldots,\lambda_n} & m_{44\lambda_1,\lambda_2,\ldots,\lambda_n} \end{pmatrix} \quad (1)$$

The above Mueller matrices of the sample are a function of the optical properties of the medium, at different incident light wavelengths. By considering interrogation of the sample at two distinct wavelengths, we can obtain the $q^{th}$ measurement of irradiance, for two images as:

$$\vec{S}_{out,\lambda_1}(q) = M_{sys}\vec{S}_{in,\lambda_1} = M_{LP2}M_{LR2}(q)M_{sample,\lambda_1}M_{LR1}(q)M_{LP1}(q)\vec{S}_{in} \quad (2)$$

$$\vec{S}_{out,\lambda_2}(q) = M_{sys}\vec{S}_{in,\lambda_2} = M_{LP2}M_{LR2}(q)M_{sample,\lambda_2}M_{LR1}(q)M_{LP1}(q)\vec{S}_{in} \quad (3)$$

where $\vec{S}_{out}(q)$ and $\vec{S}_{in}$, are the Stokes parameters at the output and input of the optical system respectively, at two wavelengths; $M_{LP1}(q)$ and $M_{LP2}(q)$ are the Mueller matrices of ideal polarizers with their transmission axes oriented along the horizontal x direction, and $M_{LR1}(q)$ and $M_{LR2}(q)$ are the Mueller matrices of the quarter wave linear retarders in the polarization state generator and the polarization state analyzer, respectively, offered elsewhere. If the Mueller matrix of the sample is not known, all the 16 elements can be determined experimentally.

Therefore, a polarimetric Mueller-matrix image difference can be defined as:

$$\begin{pmatrix} m_{11\lambda_2} & m_{12\lambda_2} & m_{13\lambda_2} & m_{14\lambda_2} \\ m_{21\lambda_2} & m_{22\lambda_2} & m_{23\lambda_2} & m_{24\lambda_2} \\ m_{31\lambda_2} & m_{32\lambda_2} & m_{33\lambda_2} & m_{34\lambda_2} \\ m_{41\lambda_2} & m_{42\lambda_2} & m_{43\lambda_2} & m_{44\lambda_2} \end{pmatrix} - \begin{pmatrix} m_{11\lambda_1} & m_{12\lambda_1} & m_{13\lambda_1} & m_{14\lambda_1} \\ m_{21\lambda_1} & m_{22\lambda_1} & m_{23\lambda_1} & m_{24\lambda_1} \\ m_{31\lambda_1} & m_{32\lambda_1} & m_{33\lambda_1} & m_{34\lambda_1} \\ m_{41\lambda_1} & m_{42\lambda_1} & m_{43\lambda_1} & m_{44\lambda_1} \end{pmatrix} \quad (4)$$

and vice versa. Therefore, a polarimetric image difference can be defined in terms of Equations 2, 3 and 4, expressed as:

$$\Delta \vec{S}_{out} = \vec{S}_{out,\lambda_2}(q) - \vec{S}_{out,\lambda_1}(q) = M_{sys}\vec{S}_{in,\lambda_2} - M_{sys}\vec{S}_{in,\lambda_1} \quad (5)$$

or in general, in terms of the Mueller matrix of the sample, $$\begin{bmatrix} S_0 \\ S_1 \\ S_2 \\ S_3 \end{bmatrix}_{OUT_{\lambda_2}} - \begin{bmatrix} S_0 \\ S_1 \\ S_2 \\ S_3 \end{bmatrix}_{OUT_{\lambda_1}} = \tag{6}$$

$$\begin{pmatrix} m_{11\lambda_2} & m_{12\lambda_2} & m_{13\lambda_2} & m_{14\lambda_2} \\ m_{21\lambda_2} & m_{22\lambda_2} & m_{23\lambda_2} & m_{24\lambda_2} \\ m_{31\lambda_2} & m_{32\lambda_2} & m_{33\lambda_2} & m_{34\lambda_2} \\ m_{41\lambda_2} & m_{42\lambda_2} & m_{43\lambda_2} & m_{44\lambda_2} \end{pmatrix} \begin{bmatrix} S_0 \\ S_1 \\ S_2 \\ S_3 \end{bmatrix}_{IN_{\lambda_2}} -$$

$$\begin{pmatrix} m_{11\lambda_1} & m_{12\lambda_1} & m_{13\lambda_1} & m_{14\lambda_1} \\ m_{21\lambda_1} & m_{22\lambda_1} & m_{23\lambda_1} & m_{24\lambda_1} \\ m_{31\lambda_1} & m_{32\lambda_1} & m_{33\lambda_1} & m_{34\lambda_1} \\ m_{41\lambda_1} & m_{42\lambda_1} & m_{43\lambda_1} & m_{44\lambda_1} \end{pmatrix} \begin{bmatrix} S_0 \\ S_1 \\ S_2 \\ S_3 \end{bmatrix}_{IN_{\lambda_1}}$$

This invention can be applied to any theoretical or experimental technique that generates a full-16 element Mueller matrix, which relates the output Stokes parameters to the input Stokes parameters.

For instance, there are several experimental/computational techniques for generating the full-16 element Mueller matrix. As an example, the Dual-Phase Retarder Rotating Retarder Mueller Matrix Polarimeter Technique, allows a complete measurement of all sixteen Mueller matrix elements through the Fourier analysis of the single detected signal. Another example is a Data Reduction technique, which can be applied to any configuration of a Mueller matrix polarimeter. Further imaging information of the target can also be obtained by applying the Mueller matrix polar decomposition of the images at different wavelengths and forming their image differences at at least two different wavelengths. Subtraction of the diattenuation, retardance, depolarization power, and birefringence at distinct wavelengths, under multi-spectral interrogation of the target can provide insightful structural and physiological information based on the difference of the attenuation of amplitude of the incident light, phase change difference, depolarizing potential of the target difference, and phase shift difference, due to the variation of index of refraction, obtained at least two distinct wavelengths, respectively. Experimentally, there are several approaches to measure the Stokes parameters utilizing the Mueller matrix formalism, namely: the "Classical Measurement Method-the Quarter-Wave", the "Measurement of the Stokes parameters Method using a Circular Polarizer", the "Fourier Analysis using a Rotating Quarter-Wave Retarder Method", the "Rotating Retarder Polarimeter based on the Polarimetric Measurement Matrix Method", and others.

Similarly, by setting a rotating-retarder polarimeter configuration (transmitter retarder at a fixed position), at least 16 individual polarization-state measurements (intensity measured values) are obtained one at every fixed angle of rotation of the receiver one-quarter retarder. Given this, a polarization measurement matrix be obtained, and the Stokes vectors can be obtained from the pseudo-inverse polarimetric measurement matrix, and polarization-state measurements intensity measured values (images) via the data reduction matrix.

A more specific/alternative example is as follows. For instance, the Rotating Retarder Polarimeter, which is based on the Polarimetric Measurement Matrix Method, allows one to calculate the Stokes vector, $\vec{S}_{out}(q)$, where $$\vec{S}_{out}(q) = A\vec{S} \tag{7}$$

where M is the Muller matrix describing the elements of the analyzer polarization of the phase retarder and the polarizer in front of the detector, including instrumental polarization, and polarization sensitivity of the detector, and, $\vec{S}_{in} = (S_0, S_1, S_2, S_3)^T$ is the Stokes vector incident on the polarization state analyzer.

Assuming linearity, the output intensity at the detector, i, is proportional to the incident intensity, according to:

$$i = \vec{A} \cdot \vec{S}_{inc} = a_0 s_0 + a_1 s_1 + a_2 s_2 + a_3 s_3 \tag{8}$$

where $\vec{A} = (a_0\ a_1\ a_2\ a_3)^T$ is an analyzer operator vector analogous to the Stokes vector.

The incident Stokes vector, $\vec{S}_{inc}$, on the polarization state analyzer, is determined by making a series of measurements $i_q$, changing the elements of the polarization state analyzer for each measurement. The intensity of the $q^{th}$ measurement is generally expressed as $$i_q = \vec{A}_q \cdot \vec{S}_{inc} \tag{8a}$$

where $\vec{A}_q$ is the analyzer operator vector for the $q^{th}$ measurement. In general, the corresponding light intensities at the output of the detector, for Q measurements, are:

$$\begin{pmatrix} i_0 \\ i_1 \\ \vdots \\ i_{Q-1} \end{pmatrix} = \begin{pmatrix} a_{00} & a_{01} & a_{02} & a_{03} \\ a_{10} & a_{11} & a_{12} & a_{13} \\ \vdots & & & \\ a_{(Q-1)0} & a_{(Q-1)1} & a_{(Q-1)2} & a_{(Q-1)3} \end{pmatrix} \begin{pmatrix} s_0 \\ s_1 \\ s_2 \\ s_3 \end{pmatrix} \tag{9}$$

where $a_{qj}$ is the $j^{th}$ element of $\vec{A}_q$ for the $q^{th}$ measurement, where (j=0,1,2,3), indicating the four Stokes parameters. Therefore, $$\vec{I}_q = W\vec{S}_{inc} \tag{10}$$

where W is the polarimetric measurement matrix. Once the polarimetric measurement matrix is known, the estimated Stokes vector $\overline{R}$ can be deduced from the inverse of that matrix and, the measured intensities, through the polarimetric data reduction equation 8:

$$\vec{R} = W^{-1}\vec{I} + U\vec{I} \tag{11}$$

where U is the polarimetric data reduction matrix. The rows of W are the coefficients of $S_0$, $S_1$, $S_2$, and $S_3$, and I is the detected intensity for a sequence of polarization optics positions.

The degree of polarization (DOP), degree of linear polarization (DOLP), degree of circular polarization (DOCP), ellipticity, and orientation also can be estimated in terms of Stokes parameters, as $$DOP = \frac{(S_1^2 + S_2^2 + S_3^2)^{1/2}}{S_0} \tag{12}$$

-continued $$DOLP = \frac{(S_1^2 + S_2^2)^{1/2}}{S_0} \quad (13)$$

$$DOCP = \frac{S_3}{S_0} \quad (14)$$

$$e = \frac{b}{a} = \frac{s_3}{s_0 + \sqrt{s_1^2 + s_2^2}} \quad (15)$$

$$\eta = \frac{1}{2}\arctan\left[\frac{s_2}{s_1}\right] \quad (16)$$

$$\varepsilon = \sqrt{1 - e^2} \quad (17)$$

and $S_0$, $S_1$, $S_2$, $S_3$ are the Stokes vectors, e, $\eta$, and $\epsilon$ are the ellipticity, azimuth, and eccentricity, respectively. The Muller-based polarimetric images, should exhibit superior imaging characteristics, due to the complete polarimetric description of the target. In general, multiple wavelengths can be utilized to interrogate the target. Furthermore, polar decomposition of the acquired Mueller matrix images can provide images of depolarization intensity, diattenuation intensity, and phase retardance.

The present invention relies in part on the following relationships: subtraction of two Mueller matrix polarimetric images $M_{\lambda 1}$, $M_{\lambda 2}$ of a target, structure and/or sample, obtained at least two distinct wavelengths $\lambda_1$, $\lambda_2$:

| | |
|---|---|
| $M_{\lambda 2} - M_{\lambda 1}$ | [1] Mueller matrix of the target (M) |
| $D_2 - D_1$ | [2] Diattenuation of the target (D) |
| $M_{D\lambda 2} - M_{D\lambda 1}$ | [3] Diattenuation matrix ($M_D$) |
| $M_{R\lambda 2} - M_{R\lambda 1}$ | [4] Retardance matrix ($M_R$) |
| $M_{\Delta\lambda 2} - M_{\Delta\lambda 1}$ | [5] Depolarizing matrix ($M_\Delta$) |
| $\delta_{\lambda 2} - \delta_{\lambda 1}$ | [6] Birefringence ($\delta$) |
| $S_{j\lambda 2} - S_{j\lambda 1}$ | [7] Stokes Parameters ($S_j$), where j = 0, 1, 2, 3 |
| $(DOP)_{\lambda 2} - (DOP)_{\lambda 1}$ | [8] Degree of polarization (DOP) |
| $(DOLP)_{\lambda 2} - (DOLP)_{\lambda 1}$ | [9] Degree of linear polarization (DOLP) |
| $(DOCP)_{\lambda 2} - (DOCP)_{\lambda 1}$ | [10] Circular polarization (DOCP) |
| $(e)_{\lambda 2} - (e)_{\lambda 1}$ | [11] Ellipticity |
| $(\eta)_{\lambda 2} - (\eta)_{\lambda 1}$ | [12] Azimuth |
| $(\epsilon)_{\lambda 2} - (\epsilon)_{\lambda 1}$ | [13] Eccentricity. |

(the order of the above operations can be reversed (i.e., $\lambda 1$-$\lambda 2$)), where subscripts 1 and 2 refer to any Mueller matrix matrices, in one instance polarimetric matrices, acquired through multi-spectral interrogation of the target with wavelengths $\lambda_1$ and $\lambda_2$, respectively, chosen from a spectrum $\lambda_1, \ldots \lambda_n$. Any number of Mueller matrices can be generated using the appropriate number of interrogating wavelengths (e.g., n Muller matrices can be generated using n interrogating wavelengths). By subtracting the 16 Mueller matrix elements of one matrix, acquired at one wavelength, one by one from those acquired at one or more different wavelengths (e.g., $m_{11\lambda 2} - m_{11\lambda 1}$) and so on, significant information regarding the nature of the target can be achieved. In general, multiple wavelengths can be utilized to interrogate the target. Further exploitation and arithmetic manipulation of S0, S1, S2, S3, obtained at different wavelengths, such as subtraction, addition, multiplication, division or combination thereof, can enhance the image process, giving rise to Stokes polarization parameters differences and the like.

The foregoing relationships can be further manipulated to enhance birefringence properties of the target; enhance diattenuation properties of the target; enhance depolarization intensity contrast; maximize spectral and energy information of the target and the surroundings; reduce interfering structures or background, leading therefore to: enhance detectability; target, structure and/or sample identification, discrimination, and classification; enhanced contrast and spatial resolution; specificity of targets embedded in turbid media, cluttered targets or samples embedded or surrounded by complex surroundings, low-contrast targets or samples, or under harsh illumination conditions such as very low/very strong light illumination or mixed light conditions, and background.

These imaging principles can be applied towards the space exploration. Existing robotic vision systems employed for space applications and planetary exploration, except for laser systems, depend on uncontrolled and variable solar illumination as well as on the thermal status of the terrain. As a result, there is a great variability in the spectral signature detected that has a major impact on image quality. In addition, extended operation of the rovers on the planetary surface, lunar or Martian, during prolonged periods of profound darkness, require some kind of artificial illumination. Therefore, the proposed technology may enhance the robotic vision in space. Specifically, it will enhance: the ability of 3D stereovision and scanning systems to perform rapid and reliable inspections of spacecraft structures, such as thermal protection insulation tiles, while at the same time using spectroscopy to detect the presence of anomalous spacecraft contaminants in 3 dimensions; the ability of robotic rovers near, or on the landing site of planetary surfaces to assess the morphology, composition, and physical and geochemical properties of the region; the exploration of powerful combined spectroscopic/microscopy imaging techniques to search for evidence of water, and life components such as proteins.

Similarly, multi-spectral Mueller matrix polarimetric imaging differences appear appealing to the medical diagnosis, and treatment. Classical imaging techniques are less than ideal tools for cancer diagnosis and assessment. Specifically, conventional x-ray imaging systems produce images based on the structure of the tissue; and thus, the resulting signal provides only anatomical information, without any physiological or metabolic signature. On the other hand, ultrasound imaging, magnetic resonance imaging (MRI), and computed tomography imaging (CT) rely basically on the ability to differentiate the tumor against the surrounding tissue and inherent background noise. As a result, they can produce signals with little sensitivity or specificity. For the latter technologies, signals are a function of cell density and micro calcifications rather than a signature of cancer per se. Interestingly enough, hepatic parenchymal scars or peritoneal fibrosis cannot be radiologically distinguished after tumor treatment. Similarly, due to osteogenic effects, in some clinical cases bone scans can exaggerate the benefits of chemotherapy, giving rise to false clinical pictures. More sensitive and specific imaging can play an important role in the diagnosis and treatment of cancer. Better imaging allows diagnosis and therapy to be addressed selectively to the tumor, and can be used to better facilitate localized surgical interventions, such as ablation, endoscopy, and lumpectomy, that allow limited diseased areas to be treated more drastically. Better imaging can also facilitate minimally invasive monitoring of therapeutic response. Developing high specificity and high sensitivity imaging technologies will assist oncologists in developing gene-to-gene receptor-specific therapies, earlier cancer diagnosing, choosing stage-specific treatment options, and accurate assessment and follow-up. Since, the multi-fusion, multi-spectral, polarimetric imaging can provide both anatomical and physiological or metabolic information, the may play an important role to the development of imaging technologies with enhanced specificity and sensitivity, capable of identifying the presence versus absence of cancer, as well as the stage, distribution, and type of cancer.

In yet another embodiment, the multi-spectral Mueller matrix/Stokes parameters polarimetric multi-wavelength difference can be combined with the addition of fluorophores, quantum dots, nanoparticles, and nanostructures to enhanced the imaging process of tissue, nanoparticle, genes, proteins, enzymes, microbes, bacteria and viruses, or single-molecule imaging, by developing high-contrast, high spatial, high-specificity, fluorescence imaging techniques, such as spatial filtering, spectral filtering, confocal microscopy, Spatially resolved, localized spectroscopy, time resolved Fluorescence Lifetime Imaging (FLIM), Fluorescence Resonance Energy Transfer (FRET), Near-Field Microscopy (NSEM), increasing the metabolic, physiological, and functional imaging information, significantly.

Similarly, the multi-spectral Mueller matrix/Stokes parameters polarimetric imaging differences can be applied for surface and subsurface imaging, inspection, characterization, classification, and monitoring of nanostructures and nanoparticles, MEMS, wafers and masks for the microelectronic industry, and optical storage devices. With feature sizes becoming increasingly smaller and 300 mm wafers being adopted and deployed in fabrication, wafer and mask inspection systems become of primary importance. Enhanced detection of semiconductor wafer defects has always been a challenge in the semiconductor manufacturing industry. Usually a semiconductor has a large number of defects such as swirls, spheres, clusters or random particles, surface defects such as scratches, voids, de-lamination, residual resist, cracks, masking errors, particles or damage which could have occurred during the manufacturing process. The detection of defects of a wafer at an early stage of the manufacturing semiconductor process can allow for possible wafer rework that can increase yields and reduce manufacturing cost. A wafer inspection implemented in the fabrication at final stages identifies all these harmful defects. The potential of this invention can be expanded not only in the study of bulk imaging, but also at single molecule/ion level, by using suitable microscopic, fluorescent imaging techniques.

Multi-fusion, multi-spectral, multi-wavelength energy matrix polarimetric imaging may play a leading role in homeland security and defense. For instance, detection of soft targets such as gas clouds containing chemical or biological warfare agents, or missile or aircraft plumes, can be enhanced dramatically through dual-energy Mueller matrix based, multi-fusion, polarimetric imaging. Typical applications of the multi-spectral, multi-fusion, dual energy Mueller matrix based polarimetric imaging could involve scenes with targets covered with camouflage net, targets hidden under trees, or target embedded in fog or subject to adverse atmospheric conditions, explosive detection, and cargo inspection, in conjunction with other soft/hard radiation modalities, and countermeasures, underwater imaging, mine detection, and other. As a result, enhanced target recognition, identification, and surveillance, could result, as well as it may be also used in a standoff battlefield surveillance platform to indicate an early warning of mass destruction weapons attacks.

The present invention can be used in transmission mode in combination with other transmission techniques, such as spatial filtering, confocal microscopy, time domain (time gating) and frequency domain techniques. Similarly, the present invention can be used in backscatter mode, and in combination with spatial filtering confocal microscopy, interferometric, optical coherence tomography.

The multi-spectral, multi-fusion, polarimetric system can utilize tunnable lasers from UV to IR, coherent or partially coherent light sources, LED's, or polychromatic light sources (white light sources), whose spectral transmission can be electronically controlled by applying voltage, acoustic signal, etc. Spectral tunability could be achieved in a number of ways, such as liquid crystal tunable filters (LCTF)'s based on birefringence, acousto-optical tunable filters (AOTF)'s based on diffraction, used as band pass tunable filters, capable to select any wavelength over wide range, as well as interferometer type filters, and others. In addition, the same filters could introduce polarization and variable phase retardation, both on the transmitting and receiving side, in combination with other material. As a result, the multi-spectral, multi-fusion, dual-energy Mueller matrix polarimetric system would be design in a way that contains no moving parts.

The multi-spectral, multi-fusion, Mueller matrix polarimetric system could be combined with a spectro-polarimeter/hyperspectral system as well as with a microscope, operating on active/passive detection principles, or in conjunction with other imaging modalities, so that to provide both bulk imaging information, spectroscopical information, and single molecule imaging capabilities. As a result, this leads to the design of a new class of multi-fusion, multifunctional imaging devices with enhanced imaging capabilities.

This invention can be utilize any set of receivers or combination of them, such as CCD cameras, CMOS, photodetectors, photomultiplies, image intensifiers, RF and microwave antennas, in combination to sensitive electronic techniques, such as autodyne, autobalance, heterodyne and superheterodyne detection techniques, and others.

The present invention can be implemented with an FPGA or other suitable computational platform (for fast real-time processing), programmed with fuzzy logic-committee neural networks for background or false rejection and target enhancement, as well as wavelet transforms for de-noising. In addition, hybrid fuzzy neural committee networks could be used to provide the optimal wavelengths for the adaptive multiwavelength energy laser beam or light source. The system can be trained to provide the optimal wavelengths for the multi-spectral optical-energy laser. Several decision fusion techniques will be investigated to fuse the decision of the member networks of committees (FCN).

A Fluorescence Near-Field Microscope (NSEM) or a NSEM could operate on multi-spectral Mueller matrix/Stokes parameters multi-wavelength polarimetric difference image principles. It could operate alone, or in conjunction to an atomic force microscope, confocal microscope, and/or any other microscopy system, spectro-polarimetric, and/or hyperspectral system.

Interrogation of the target by means of multi-spectral wavelengths for multi-spectral total internal reflection reflection microscopy.

An optical computed tomography CT/dual energy CT, planar tomographic system, tomosynthesis. It could provide excellent contrast resolution, the slice thickness could be selected based on the wavelength difference of the interrogating wavelengths (the smaller wavelength difference would provide better resolution).

The present invention may also be utilized for/adapted to:
Efficient single molecule multi-spectral imaging,
Cancer detection, tumor detection (e.g., melanoma detection),
Ophthalmology imaging, imaging of a retina,
Enhanced active-passive optical polarimetric imaging systems, High-contrast enhanced specificity nano-imaging techniques for clinical, nanotechnology, and microelectronic applications, High-resolution nano-imaging instrumentation with integrated capabilities, Accurate imaging of nanostructures and nano-devices, Efficient molecular imaging signatures, Micro- and nano-imaging of small dimension devices, semiconductor wafers, and high complexity microelectronic circuits, Enhanced imaging of wafer allowing detection of defects in semiconductor components and microelectronic structures, High resolution clinical nano-imaging devices, Biophotonics and molecular imaging, Quantum dot and nanophore bio-imaging, Imaging of nano-structured molecular architectures, Clinical nano-imaging, detection, identification and classification of cellular modulating mechanisms and agents, High resolution enhanced specificity and sensitivity optical imaging technologies and techniques for clinical diagnosis and assessment, Physiological imaging techniques for early cancer detection, assessment and follow-up, Enhanced digital radiography and tomography for medical imaging, Advanced multimodality imaging technologies, Efficient inspection, characterization, classification, and monitoring of wafers and masks for the microelectronic industry, Other industrial applications, Enhanced polarimetric multi-spectral imaging sensor platforms for rover navigation and rapid and reliable repair of spacecraft structures, High sensitivity, high specificity powerful spectroscopic nano-imaging techniques for exploration of planetary resources, Multi-spectral and hyperspectral multi-fusion optical polarimetric imaging platforms, Active and passive spectroscopic imaging combined with nano-imaging technologies, Multimodality imaging platforms, Airport security in combination with other multifunctional modalities, Explosive detection, Countermeasures, Cargo Security in combination with other multifunctional imaging modalities, Underwater target detection and imaging in combination with other multifunctional imaging modalities, such as ultrasound, RF, or others, Biochemical detection, Infrastructure protection, Technologies for efficient detection under harsh environments, Multi-spectral and hyperspectral multi-fusion optical polarimetric imaging platforms, Active and passive spectroscopic imaging technologies, Multimodality imaging platforms, Multi-density, multimedia, multi-atomic X-ray dual energy technologies, Intelligent surveillance and reconnaissance integrated platforms, Innovative multimedia, multi-atomic number, multi-density, dual energy systems for enhanced digital X-ray scanning imaging, Multi-fusion, multi-spectral, integrated optical polarimetric platforms for enhanced high contrast, high specificity imaging, Target identification and recognition, Target characterization and assessment, Missile signatures, Countermeasures, Underwater detection, Mine detection, Battlefield imaging, Multi-spectral and hyperspectral multi-fusion optical polarimetric imaging platforms, Active and passive spectroscopic imaging technologies, Multimodality imaging platforms, Multi-density, multimedia, multi-atomic X-ray dual energy technologies, and Intelligent surveillance and reconnaissance integrated platforms.

The invention can be used in combination of active/passive target interrogation techniques. The advantages of an active interrogation technique (laser beams, LED's) are:

Improved image quality over a wide range of imaging sensing platforms because:

The light excitation of the target and the reflected light spectra are both independent of variable and unpredictable sun illumination or target/background temperature. As a result, active systems require detection of much narrower spectral bands than passive systems because the signatures have less variability due to time-varying signature properties such as sun illumination.

The ability to characterize the state of polarization of radiation from each pixel of a target scene by measuring all four components of the Stokes vector, from the 16 Mueller matrix elements, as a function of wavelength to yield high contrast resolution, high spatial resolution, and specificity images.

The invention comprises multiwavelength-energy polarimetric imaging capabilities. A weighted subtraction of the low energy and the high energy polarimetric images can remove background structures or interfering cluttered events.

Further image enhancement can be achieved by subtracting degree of linear polarization images (DOLP)s obtained at low and high photon energies.

The fact that, signal processing occurs naturally at the front end electronics (detector), through application of the dual-energy polarimetric principles, minimizes the use of onboard processing.

The proposed polarimetric, dual-energy, multi-spectral imaging is light photon quantum noise limited, and exhibits higher contrast and specificity than current passive sensing imaging technology or laser-based systems alone.

Unlike current technology, the proposed technology will provide enhanced images in adverse weather/environmental conditions.

The acquired images provide information related to the target material composition as well as to the morphology of the target.

The spectral distribution of the illuminating lasers can be tuned to interrogate a specific target and proviode unique, spectral, energy, polarimetric amplitude and phase contrast information.

Various modifications and alterations that do not depart from the scope and spirit of this invention will become apparent to those skilled in the art. This invention is not to be duly limited to the illustrative embodiments set forth herein.

What is claimed is:

1. A multi-energy polarization imaging system comprising:
   (a) at least one energy source for irradiating a target with at least one quantity of light and at least one quantity of non-light energy, the at least one quantity of light comprising at least one wavelength of light and the at least one quantity of non-light energy comprising at least one wavelength of non-light energy, wherein the wavelength of the non-light energy is either shorter or longer than the wavelength of the at least one quantity of light;
   (b) a polarization-state generator for generating a polarization state for each quantity of light, the polarization-state generator comprising at least one polarizer, each polarizer being adapted to polarize an individual wavelength before the one or more quantities of light enter a first waveplate;
   (c) a polarization-state receiver for evaluating a resulting polarization state of each of the one or more quantities of light following illumination of the target, the polarization-state receiver comprising a second waveplate through which the one or more quantities of light are transmitted before entering at least one second polarizer;
   (d) an image-capture device for capturing at least a first image and a second image of the target irradiated by the at least one quantity of light and the at least one quantity of energy, the first image corresponding to an image of the target generated from the wavelength of light and the second image corresponding to an image of the target generated from the wavelength of energy; and
   (e) a processing unit for assigning a weighting factor to at least one of the first and second images and evaluating a weighted difference between the first and second images to generate a multi-wavelength image of the target.

2. The system according to claim 1, wherein the first waveplate is a one-quarter (¼) waveplate.

3. The system of claim 1, wherein the second waveplate is a one-quarter (¼) waveplate.

4. The systems of claim 1, wherein both the first and second waveplates are one-quarter (¼) waveplates.

5. A multi-energy polarization imaging system comprising:
   (i) at least one light source for illuminating a target with at least one quantity of light, the at least one quantity of light comprising at least two wavelengths of light, a first wavelength and a second wavelength, the second wavelength being different than the first wavelength;
   (ii) a polarization-state generator for generating a polarization state for each quantity of light, the polarization-state generator comprising at least two polarizers, each polarizer being adapted to polarize an individual wavelength before the one or more quantities of light enter at least one first waveplate;
   (iii) a polarization-state receiver for evaluating a resulting polarization state of each of the one or more quantities of light following illumination of the target, the polarization-state receiver comprising at least one second waveplate through which the one or more quantities of light are transmitted before entering at least one second polarizer;
   (iv) an image-capture device for capturing at least a first image and a second image of the target illuminated by the at least one quantity of light, the first image corresponding to an image of the target generated from the first wavelength component of the at least one quantity of light and the second image corresponding to an image of the target generated from the second wavelength component of the at least one quantity of light; and
   (v) a processing unit for assigning a weighting factor to at least one of the first and second images and evaluating a weighted difference between the first and second images to generate a multi-wavelength image of the target,
   wherein the processing unit comprises an artificial fuzzy neural network that uses information stored in the computer readable memory to determine a suitable wavelength for each quantities of light for the condition at a time when the multi-energy image is to be generated.

6. The system according to claim 5, wherein at least one light source is used in combination with the at least one energy source, the at least one energy source being adapted to generate one or more wavelengths of energy in the gamma ray, X-ray, ultraviolet ray, infrared ray, radar, RE, microwaves, terahertz waves, and/or radio wave portions of the electromagnetic spectrum.

7. The system according to claim 5, wherein there is one light source and the light source is capable of simultaneously generating a quantity of light having at least two discrete wavelengths of light.

8. The system according to claim 5, wherein there is one light source and the light source is capable of sequentially generating a quantity of light having at least two discrete wavelengths of light.

9. The system according to claim 5, wherein there is at least two light sources and each light source is capable of generating a quantity of light having one discrete wavelength of light.

10. The system according to claim 5, wherein the image-capture device is a light image-capture device.

11. The system according to claim 10, wherein the light image-capture device is an electro-optical device.

12. The system according to claim 11, wherein the electro-optical device is positioned in optical alignment with the polarization-state receiver to capture the first and second images.

13. The system according to claim 5, wherein the at least one light source comprises at least one laser.

14. The system according to claim 5, wherein the at least one light source is configured to emit energy in a planar geometry, fan-beam geometry, pointwise irradiation, or any combination thereof.

15. The system according to claim 5, wherein the first and second waveplates are each a quarter-wave retarder.

16. The system according to claim 15, wherein the quarter-wave retarders forming the first and second waveplates are rotated at an angular-velocity ratio of 5:1.

17. The system according to claim 5, wherein the polarization-state generator and the polarization-state receiver are generally linearly aligned on opposite sides of the target.

18. The system according to claim 5, wherein the polarization-state receiver is positioned to evaluate the resulting polarization state of each quantity of light reflected by the target.

19. The system according to claim 5, further comprising a computer readable memory for storing information to be used by the processing unit for determining a suitable wavelength for each quantity of light.

20. The system according to claim 5, wherein the image-capture device converts the first captured image into a first Mueller matrix of the target and the second captured image into a second Mueller matrix of the target in order to permit processing, comparison and/or combination of the Mueller matrices from first and second images.

21. The system according to claim 5, wherein the image-capture device converts the first captured image into a first Stokes parameter image of the target and the second captured image into a second Stokes parameter image of the target in order to permit processing, comparison and/or combination of the Mueller matrices from first and second images.

22. A multi-energy polarization imaging system comprising:
(A) at least one light source for illuminating a target with at least one quantity of light, the at least one quantity of light comprising at least two wavelengths of light, a first wavelength and a second wavelength, the second wavelength being different than the first wavelength;
(B) a polarization-state generator for generating a polarization state for each quantity of light, the polarization-state generator comprising at least one polarizer, each polarizer being adapted to polarize an individual wavelength before the one or more quantities of light enter through at least one rotating one-quarter (¼) waveplate linear retarder;
(C) a polarization-state receiver for evaluating a resulting polarization state of each of the one or more quantities of light following illumination of the target, the polarization-state receiver comprising at least one second rotating one-quarter (¼) waveplate linear retarder through which the one or more wavelengths of light are transmitted before entering at least one second polarizer;
(D) an image-capture device for capturing at least a first image and a second image of the target illuminated by the at least one quantity of light, the first image corresponding to an image of the target generated from the first wavelength of light and the second image corresponding to an image of the target generated from the second wavelength of light, wherein the image-capture device receives and/or generates for each of the at least first and second images at least 16 individual polarization-state measurements; and
(E) a processing unit for comparing the at least 16 individual polarization state measurements from the at least first and second images,
wherein the 16 individual polarization state measurements from each image are averaged together by the processing unit to form average polarimetris images corresponding individually to at least the first and second images.

23. The system of claim 22, wherein the first average polarimetric image of the target and the second polarmetric image of the target are subtracted from one another to obtain a weight spectral image difference of the target, wherein the first average polarimetric image corresponds to an average polarimetric image of the target generated using the data obtained at the first wavelength and the second average polarimetric image corresponds to an average polarimetric image of the target generated using the data obtained at the second wavelength.

24. The system according to claim 22, wherein the 16 individual polarization state measurements from each image are used to generate a Mueller matrix for one individual wavelength of light.

25. A method for generating a multi-modality image of a target, the method comprising the steps of:
(i) emitting at least two quantities of energy, at least one quantity of energy being a quantity of light having a first wavelength, the second quantity of energy having a second wavelength different from the first wavelength, the second wavelength being selected from a non-light wavelength;
(ii) creating an initial polarization state for at least the one quantity of light by polarizing and then retarding one component of the at least the one quantity of light relative to another component of the at least one quantity of light;
(iii) directing the at least two quantities of energy generally toward the target so that the target is irradiated by the at least two quantities of energy, including directing the polarization state of any polarized energy generally toward the target in the instance where at least a portion of the energy is polarized;
(iv) analyzing a resulting polarization state for each of the first and second quantities of energy by retarding one component of the first and second quantities of energy following irradiation of the target relative to another component of the first and second quantities of energy, and then polarizing the retarded first and second quantities of energy;
(v) capturing a first image of the target irradiated by the first quantity of energy and a second image of the target irradiated by the second quantity of energy;
(vi) weighting at least one of the first and second images; and
(vii) generating the multi-energy image of the target by evaluating a weighted difference between the first and second images, and/or by comparing and/or combining the first and second images.

26. The method according to claim 25, wherein the step of emitting the first and second quantities of energy comprises the step of:
utilizing an energy source that has the ability to generate one or more wavelengths of energy in the gamma ray, X-ray, ultraviolet ray, visible, infrared ray, radar, terahertz waves, and/or radio wave portions of the electromagnetic spectrum.

27. The method according to claim 25, wherein the step of creating an initial polarization state comprises the steps of:
linearly polarizing the first and second quantities of energy; and
then retarding at least one of the ordinary and extraordinary components of the linearly-polarized energy with a quarter-wave retarder to create a phase angle between the ordinary and extraordinary components.

28. The method according to claim 25, wherein the step of analyzing the resulting polarization state comprises the steps of:
analyzing a resulting phase angle between the ordinary and extraordinary components of the first and second quantities of energy following interaction of the first and second quantities of energy with the target; and
then linearly polarizing the first and second quantities of energy.

29. The method according to claim 25, wherein the step of weighting at least one of the first and second images comprises the steps of:
determining a Mueller matrix for each of the first and second images;
determining a weighting factor suitable for at least one of the first and second images; and
changing at least one of the first and second images by the value of the weighting factor.

30. The method according to claim 25, wherein the step of generating the multi-energy image of the target comprises the steps of:
determining a difference between the at least one weighted image and the remaining image;
generating a Mueller matrix for the difference between the two images; and
displaying an image generated from the Mueller matrix for the difference between the two images.

* * * * *